United States Patent
Bowman

(10) Patent No.: US 11,724,050 B2
(45) Date of Patent: Aug. 15, 2023

(54) HUMIDIFICATION SYSTEM AND POSITIVE AIRWAY PRESSURE APPARATUS INCORPORATING SAME

(71) Applicant: SOMNETICS INTERNATIONAL, INC., Fridley, MN (US)

(72) Inventor: Bruce Bowman, Eden Prairie, MN (US)

(73) Assignee: SOMNETICS INTERNATIONAL, INC., Fridley, MN (US)

( * ) Notice: Subject to any disclaimer, the term of this patent is extended or adjusted under 35 U.S.C. 154(b) by 352 days.

(21) Appl. No.: 16/997,066

(22) Filed: Aug. 19, 2020

(65) Prior Publication Data

US 2020/0376215 A1   Dec. 3, 2020

Related U.S. Application Data

(62) Division of application No. 14/571,479, filed on Dec. 16, 2014, now abandoned.

(60) Provisional application No. 61/916,959, filed on Dec. 17, 2013.

(51) Int. Cl.
| | |
|---|---|
| A61M 16/00 | (2006.01) |
| A61M 16/10 | (2006.01) |
| A61M 16/16 | (2006.01) |

(52) U.S. Cl.
CPC .... *A61M 16/0069* (2014.02); *A61M 16/0051* (2013.01); *A61M 16/026* (2017.08); *A61M 16/109* (2014.02); *A61M 16/16* (2013.01); *A61M 16/161* (2014.02); *A61M 2205/15* (2013.01); *A61M 2205/18* (2013.01); *A61M 2205/3368* (2013.01); *A61M 2205/3386* (2013.01); *A61M 2205/502* (2013.01); *A61M 2205/581* (2013.01); *A61M 2205/583* (2013.01)

(58) Field of Classification Search
CPC .......................... A61M 16/109; A61M 16/161
See application file for complete search history.

(56) References Cited

U.S. PATENT DOCUMENTS

| | | | |
|---|---|---|---|
| 3,721,233 | A | 3/1973 | Montgomery et al. |
| 4,010,748 | A | 3/1977 | Dobritz |
| 4,381,267 | A | 4/1983 | Jackson |
| 4,396,015 | A | 8/1983 | Johnson |

(Continued)

FOREIGN PATENT DOCUMENTS

| | | |
|---|---|---|
| BE | 439 032 A | 9/1940 |
| EP | 0 601 708 B1 | 3/2000 |
| EP | 1 655 052 A2 | 5/2006 |
| FR | 2695320 A1 | 3/1994 |

(Continued)

OTHER PUBLICATIONS

U.S. Appl. No. 61/916,959, filed Dec. 17, 2013, Bowman.

(Continued)

*Primary Examiner* — LaToya M Louis
(74) *Attorney, Agent, or Firm* — Mueting Raasch Group

(57) ABSTRACT

Systems, apparatus, and methods for providing humidity in a positive airway pressure (PAP) device. In one embodiment, a humidifier is configured to periodically provide vapor to a flow of pressurized gas to produce flows of pressurized gas with added humidity. Each of the flows of pressurized gas with added humidity may be timed to reach a user interface primarily during a first portion of a breath cycle (e.g., during inspiration). Portions of the flow of pressurized gas that reach the user interface during a second portion of the breath cycle (e.g., during expiration) may include little or no added humidity.

9 Claims, 23 Drawing Sheets

(56) References Cited

U.S. PATENT DOCUMENTS

| | | |
|---|---|---|
| 4,644,947 A | 2/1987 | Whitwam et al. |
| 4,829,998 A | 5/1989 | Jackson |
| 4,955,372 A | 9/1990 | Blackmer et al. |
| 5,054,484 A | 10/1991 | Hebeler, Jr. |
| 5,349,946 A | 9/1994 | McComb |
| 5,551,419 A | 9/1996 | Froehlich et al. |
| RE35,339 E | 10/1996 | Rapoport |
| 5,655,522 A | 8/1997 | Meehlenburg et al. |
| 5,657,752 A | 8/1997 | Landis et al. |
| 5,673,687 A | 10/1997 | Dobson |
| 5,692,095 A | 11/1997 | Young |
| 5,769,071 A | 6/1998 | Turnbull |
| 5,845,636 A | 12/1998 | Gruenke et al. |
| 5,870,525 A | 2/1999 | Young |
| 5,937,855 A | 8/1999 | Zdrojkowski et al. |
| 5,954,050 A | 9/1999 | Christopher |
| 5,964,219 A | 10/1999 | Pekka |
| 6,050,260 A | 4/2000 | Daniell et al. |
| 6,095,505 A | 8/2000 | Miller |
| 6,102,037 A | 8/2000 | Koch |
| 6,162,046 A | 12/2000 | Young et al. |
| 6,347,936 B1 | 2/2002 | Young et al. |
| 6,435,180 B1 | 8/2002 | Hewson et al. |
| 6,523,538 B1 | 2/2003 | Wikefeldt |
| 6,532,960 B1 | 3/2003 | Yurko |
| 6,554,260 B1 | 4/2003 | Lipscombe et al. |
| 6,585,509 B2 | 7/2003 | Young et al. |
| 6,634,864 B1 | 10/2003 | Young et al. |
| 6,644,316 B2 | 11/2003 | Bowman et al. |
| D483,869 S | 12/2003 | Tran et al. |
| 6,679,265 B2 | 1/2004 | Strickland et al. |
| 6,694,978 B1 | 2/2004 | Bennarsten |
| 6,766,800 B2 | 7/2004 | Chu et al. |
| D497,379 S | 10/2004 | Tran et al. |
| D498,768 S | 11/2004 | Romandy et al. |
| 6,854,465 B2 | 2/2005 | Bordewick et al. |
| 6,935,337 B2 | 8/2005 | Virr et al. |
| 6,976,489 B2 | 12/2005 | Mantell et al. |
| 7,063,086 B2 | 6/2006 | Shahbazpour et al. |
| 7,066,174 B1 | 6/2006 | Smith et al. |
| 7,089,941 B2 | 8/2006 | Bordewick et al. |
| 7,096,864 B1 | 8/2006 | Mayer et al. |
| 7,115,097 B2 | 10/2006 | Johnson |
| 7,146,979 B2 | 12/2006 | Seakins et al. |
| 7,156,090 B2 | 1/2007 | Nomori |
| 7,244,235 B2 | 7/2007 | Bowman et al. |
| D555,235 S | 11/2007 | Korkowski et al. |
| D557,405 S | 12/2007 | Tran et al. |
| 7,302,949 B2 | 12/2007 | Pelerossi et al. |
| D558,874 S | 1/2008 | Tran et al. |
| D559,975 S | 1/2008 | Tran et al. |
| D560,794 S | 1/2008 | Tran et al. |
| 7,428,902 B2 | 9/2008 | Du et al. |
| 7,431,570 B2 | 10/2008 | Young et al. |
| 7,487,778 B2 | 2/2009 | Freitag |
| 7,516,740 B2 | 4/2009 | Meier |
| 7,525,663 B2 | 4/2009 | Kwok et al. |
| RE40,806 E | 6/2009 | Gradon et al. |
| 7,562,656 B2 | 7/2009 | Gallem et al. |
| 7,588,033 B2 | 9/2009 | Wondka |
| 7,614,398 B2 | 11/2009 | Virr et al. |
| 7,694,675 B2 | 4/2010 | Koch et al. |
| 7,814,911 B2 | 10/2010 | Bordewick et al. |
| 7,845,353 B2 | 12/2010 | Bordewick et al. |
| 7,920,777 B2 | 4/2011 | Rabin et al. |
| 7,938,113 B2 | 5/2011 | Weinstein et al. |
| 7,942,644 B2 | 5/2011 | Young et al. |
| 7,962,018 B2 | 6/2011 | Hunt et al. |
| 7,992,554 B2 | 8/2011 | Radomski et al. |
| 7,997,270 B2 | 8/2011 | Meier |
| 8,020,557 B2 | 9/2011 | Bordewick et al. |
| D648,435 S | 11/2011 | Brodbeck |
| 8,052,127 B2 | 11/2011 | Nichols et al. |
| 8,074,641 B2 | 12/2011 | Gallem et al. |
| 8,074,645 B2 | 12/2011 | Bordewick et al. |
| 8,091,553 B2 | 1/2012 | Bordewick et al. |
| 8,100,124 B2 | 1/2012 | Becker et al. |
| 8,201,752 B2 | 6/2012 | Brodbeck et al. |
| 8,206,337 B2 | 6/2012 | Blackhurst et al. |
| 8,235,041 B2 | 8/2012 | Seakins et al. |
| 8,282,084 B2 | 10/2012 | Nichols et al. |
| 8,327,845 B2 | 12/2012 | Weinstein et al. |
| 8,459,252 B2 | 6/2013 | Gallem et al. |
| 8,469,025 B2 | 6/2013 | Mayer et al. |
| RE44,453 E | 8/2013 | Virr et al. |
| 8,511,651 B2 | 8/2013 | Fridberg et al. |
| 8,544,461 B2 | 10/2013 | Gründler et al. |
| 8,602,025 B2 | 12/2013 | Bordewick et al. |
| 8,616,202 B2 | 12/2013 | Tatkov et al. |
| 8,671,936 B2 | 3/2014 | Meier |
| 8,720,439 B1 | 5/2014 | Kolkowski et al. |
| 8,733,349 B2 | 5/2014 | Bath et al. |
| 9,186,477 B2 | 11/2015 | Hunt et al. |
| 9,289,572 B2 | 3/2016 | Korneff et al. |
| 9,802,015 B2 | 10/2017 | Virr et al. |
| 2003/0079749 A1 | 5/2003 | Strickland et al. |
| 2003/0205226 A1 | 11/2003 | Gallem et al. |
| 2004/0074493 A1 | 4/2004 | Seakins et al. |
| 2004/0079370 A1 | 4/2004 | Gradon et al. |
| 2004/0226562 A1 | 11/2004 | Bordewick et al. |
| 2005/0076906 A1 | 4/2005 | Johnson |
| 2005/0205088 A1 | 9/2005 | Tran et al. |
| 2006/0037613 A1 | 2/2006 | Kwok et al. |
| 2006/0065267 A1 | 3/2006 | Tran et al. |
| 2006/0081250 A1 | 4/2006 | Bordewick et al. |
| 2006/0196968 A1 | 9/2006 | Rabin et al. |
| 2006/0231097 A1 | 10/2006 | Dougherty et al. |
| 2006/0231102 A1 | 10/2006 | Bordewick et al. |
| 2007/0277827 A1 | 12/2007 | Bordewick et al. |
| 2008/0000798 A1 | 1/2008 | Gutmann et al. |
| 2008/0006275 A1 | 1/2008 | Nickelson et al. |
| 2008/0035141 A1 | 2/2008 | Warner et al. |
| 2008/0053451 A1 | 3/2008 | Bordewick et al. |
| 2008/0072904 A1 | 3/2008 | Becker et al. |
| 2008/0099017 A1 | 5/2008 | Bordewick et al. |
| 2008/0161409 A1 | 7/2008 | Warner et al. |
| 2008/0190427 A1 | 8/2008 | Payton et al. |
| 2008/0260863 A1 | 10/2008 | Warner et al. |
| 2009/0078255 A1 | 3/2009 | Bowman et al. |
| 2009/0078258 A1 | 3/2009 | Bowman et al. |
| 2009/0110379 A1 | 4/2009 | McGhin et al. |
| 2010/0065054 A1 | 3/2010 | Bowman et al. |
| 2010/0142934 A1 | 6/2010 | Sellers et al. |
| 2011/0162647 A1 | 7/2011 | Huby et al. |
| 2011/0210458 A1 | 9/2011 | Brodbeck et al. |
| 2012/0097156 A1 | 4/2012 | Bowman et al. |
| 2012/0125334 A1 | 5/2012 | Korneff et al. |
| 2012/0167879 A1 | 7/2012 | Bowman et al. |
| 2012/0248636 A1 | 10/2012 | Fridberg et al. |
| 2013/0269693 A1 | 10/2013 | Neatrour et al. |
| 2014/0007871 A1 | 1/2014 | Bordewick et al. |
| 2014/0166006 A1 | 6/2014 | Meier |
| 2015/0165146 A1 | 6/2015 | Bowman et al. |

FOREIGN PATENT DOCUMENTS

| | | |
|---|---|---|
| WO | WO 91/19527 A1 | 12/1991 |
| WO | WO 99/21602 A1 | 5/1999 |
| WO | WO 02/085417 A2 | 10/2002 |
| WO | WO 2005/079898 A2 | 9/2005 |
| WO | WO 2006/044120 A2 | 4/2006 |
| WO | WO 2007/117716 A2 | 10/2007 |
| WO | WO 2007/120666 A1 | 10/2007 |
| WO | WO 2007/149446 A2 | 12/2007 |
| WO | WO 2010/096467 A1 | 8/2010 |
| WO | WO 2012/094230 A2 | 7/2012 |
| WO | WO 2013/124803 A1 | 8/2013 |

OTHER PUBLICATIONS

MyPurMist: Handheld Steam Inhaler, 2013. Accessed on the Internet Apr. 15, 2015: <https://web.archive.org/web/20130625073306/http://www.mypurmist.com/instant-steam-vaporizer/index.aspx>.

(56) References Cited

OTHER PUBLICATIONS

U.S. Appl. No. 14/571,479 (parent), Final Office Action dated Apr. 30, 2020.
U.S. Appl. No. 14/571,479 (parent), Nonfinal Office Action dated Aug. 22, 2019.
U.S. Appl. No. 14/571,479 (parent), Final Office Action dated Mar. 8, 2019.
U.S. Appl. No. 14/571,479 (parent), Nonfinal Office Action dated Jul. 13, 2018.

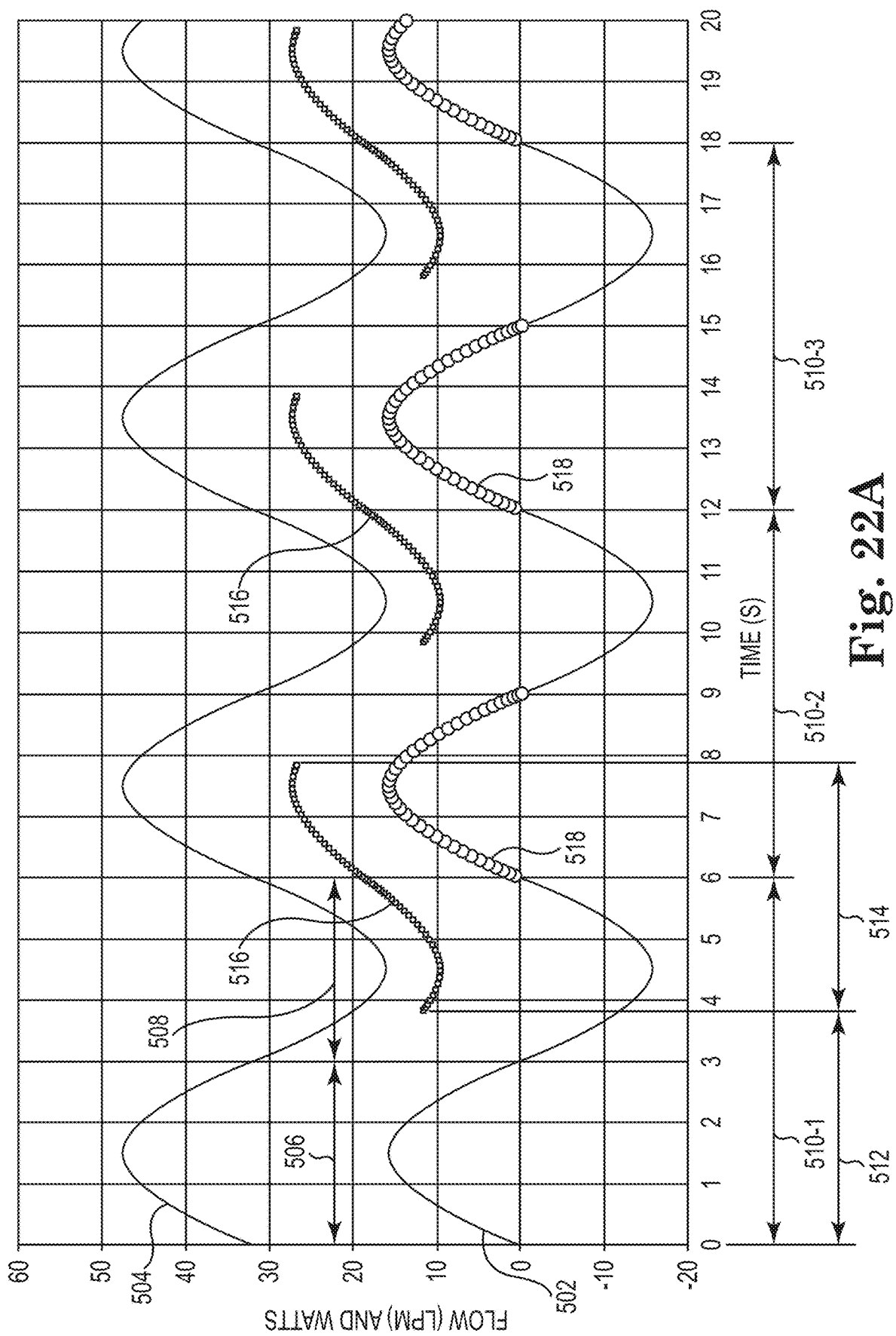

HUMIDIFICATION SYSTEM AND POSITIVE AIRWAY PRESSURE APPARATUS INCORPORATING SAME

RELATED APPLICATION(S)

This application is a divisional application of U.S. patent application Ser. No. 14/571,479, filed Dec. 16, 2014, which claims the benefit of U.S. Provisional Application No. 61/916,959, filed Dec. 17, 2013, the disclosures of which are incorporated herein by reference in their entireties.

Embodiments described herein relate generally to positive airway pressure apparatus and systems, and, more particularly, to systems and methods adapted to humidify a gas (such as air) delivered by the positive airway pressure apparatus.

BACKGROUND

Positive airway pressure (PAP) therapies are frequently used in the treatment of, among other ailments, obstructive sleep apnea, asthma, bronchitis, chronic obstructive pulmonary disease, snoring, and congestive heart failure. These therapies typically provide a flow of fluid (e.g., typically a gas such as air, but may be most any gas or gas-vapor mixture that may or may not include therapeutic agents such as oxygen, water, or medicinal vapors) to pressurize the airway of a user to a pressure in the range of 4-30 centimeters (cm) of water (e.g., often about 4-20 cm water) or more.

Depending upon the particular therapy, a variable or a constant pressure may be administered to the user to reduce or eliminate airway occlusions (or to otherwise treat acute or chronic respiratory failure) that necessitated the use of the therapy. For instance, continuous positive airway pressure (CPAP) may provide a generally continuous pressure throughout the user's breathing cycle. Bi-level positive airway pressure (Bi-PAP) may provide at least two different pressures in coordination with the user's inhalation and exhalation efforts. In more advanced systems, auto-titration positive airway pressure (Auto-PAP) systems may regulate the therapy pressure based on the level of breathing assistance the user may require at any given point during a breath.

Regardless of the particular therapy, these positive airway pressure (PAP) systems typically include at least a blower unit and a user interface or mask. A delivery hose may connect the blower unit to the mask, wherein the hose and mask together define a gas delivery conduit between the blower unit and the user.

The mask may be configured to secure relative to the user's head in such a way as to form a generally air-tight seal with the user's airway (e.g., seal about the face, nares, and/or mouth). As a result, the blower unit may generate a flow of pressurized gas that is delivered to the airway via the delivery conduit.

A humidifier for humidifying the gas provided by the blower unit may also be provided. PAP humidifiers typically include a heated water reservoir containing a volume of water with a relatively large surface area. The reservoir is positioned between the blower unit and the mask. Gas from the blower unit may pass over the reservoir, where the gas collects evaporating water. The gas with the now-entrained moisture is then, via the delivery conduit, provided to the user.

SUMMARY

In one embodiment, a positive airway pressure apparatus is provided that includes: a flow generator comprising a housing containing a blower, the blower adapted to produce a flow of pressurized gas; a user interface adapted to communicate the flow of pressurized gas to an airway during a breath cycle; and an elongate delivery tube positioned between the flow generator and the user interface, the delivery tube adapted to communicate the flow of pressurized gas from the blower to the user interface. The apparatus may also include a humidifier defining an outlet that is in communication with the flow of pressurized gas, wherein the humidifier has a vaporizing device and a water source, the outlet located between the blower and the delivery tube. An electrical power source may be provided and adapted to provide electrical power to the humidifier. A controller in communication with both the vaporizing device and the power source is also provided. The controller is adapted to automatically modulate the electrical power provided to the humidifier during the breath cycle, wherein the electrical power is modulated in proportion to a flow rate of the flow of pressurized gas such that the humidifier adds water vapor at a rate that maintains a near constant humidity level in the flow of pressurized gas during the breath cycle.

In another embodiment, a positive airway pressure apparatus is provided that includes: a flow generator having a housing containing a blower, the blower adapted to produce a flow of pressurized gas at a variable flow rate; a user interface adapted to communicate the flow of pressurized gas to an airway during a target breath cycle; and an elongate delivery tube positioned between the flow generator and the user interface, the delivery tube adapted to communicate the flow of pressurized gas from the blower to the user interface. A humidifier may also be provided and includes a vaporizing device having an outlet in communication with the flow of pressurized gas, wherein the outlet is located upstream from the user interface. An electrical power source is adapted to provide electrical power to the vaporizing device. A controller in communication with both the power source and the vaporizing device is also provided. The controller is adapted to provide the electrical power to the vaporizing device during a power interval such that the vaporizing device introduces water vapor into an inspiration portion of the flow of pressurized gas, during the power interval, to produce a flow of pressurized gas with added humidity. A start time and duration of the power interval are selected or calculated such that the flow of pressurized gas with added humidity arrives at the user interface beginning at or near an onset of an inspiratory phase of the target breath cycle and lasts for most or all of the inspiratory phase of the target breath cycle.

In yet another embodiment, a method for adding humidity to gas delivered by a positive airway pressure apparatus is provided. The method includes: producing, with a blower, a flow of pressurized gas at a variable flow rate; transporting the flow of pressurized gas from the blower to a user interface via a delivery tube positioned between the blower and the user interface; and detecting, with a controller, one or both of an inspiratory phase and an expiratory phase of one or more breath cycles. The method further includes introducing, during a power interval, humidity into a portion of the flow of pressurized gas to produce a discrete flow of pressurized gas with added humidity. The humidity is introduced by a vaporizing device having an outlet proximate the blower and in communication with the flow of pressurized gas. The method also includes determining, automatically with the controller, a start time and duration of the power interval so that the flow of pressurized gas with added humidity reaches the user interface at or near an onset of an inspiratory phase of a current or future breath cycle and ends at or near an end of the inspiratory phase, or at or near an onset of an expiratory phase, of the current or future breath cycle.

In still yet another embodiment, a method for adding humidity to gas provided by a positive airway pressure (PAP) apparatus is provided. The method includes: producing a continuous and variable flow of pressurized gas with a blower; transporting the flow of pressurized gas from the blower to a user interface via a delivery tube positioned between the blower and the user interface; and predicting, automatically with a PAP controller, a start time and duration of an inspiratory phase of a target breath cycle based upon an analysis of a current or a preceding breath cycle. The method also includes calculating or selecting, automatically with a humidification controller, a delay time and duration of a power interval, and providing power, under control of the humidification controller, to a vaporizing device after expiration of the power interval delay time, wherein the power lasts for the power interval duration. The vaporizing device is located proximate an outlet of the blower and is in communication with the flow of pressurized gas. The method also includes introducing humidity with the vaporizing device into the flow of pressurized gas during the power interval duration to produce a flow of pressurized gas with added humidity that reaches the user interface at or near an onset of the inspiratory phase of the target breath cycle and terminates at or near a beginning of an expiratory phase of the target breath cycle.

The above summary is not intended to describe each embodiment or every implementation. Rather, a more complete understanding of illustrative embodiments will become apparent and appreciated by reference to the following Detailed Description of Exemplary Embodiments and claims in view of the accompanying figures of the drawing.

BRIEF DESCRIPTION OF THE VIEWS OF THE DRAWING

Exemplary embodiments will be further described with reference to the figures of the drawing, wherein:

FIGS. 22A-22C are plots illustrating Flow versus Time and Power versus Time for simulated breathing scenarios, wherein the breathing scenarios are generally identical (e.g., same tidal volume) except for varying a PAP system pressure and a breath rate, wherein: FIG. 22A represents a system pressure of 20 centimeters (cm) of water and a breath rate of 10 breaths/minute; FIG. 22B represents a system pressure of 4 cm of water and a breath rate of 10 breaths/minute; and FIG. 22C represents a system pressure of 4 cm of water and a breath rate of 15 breaths/minute.

Figure 1:
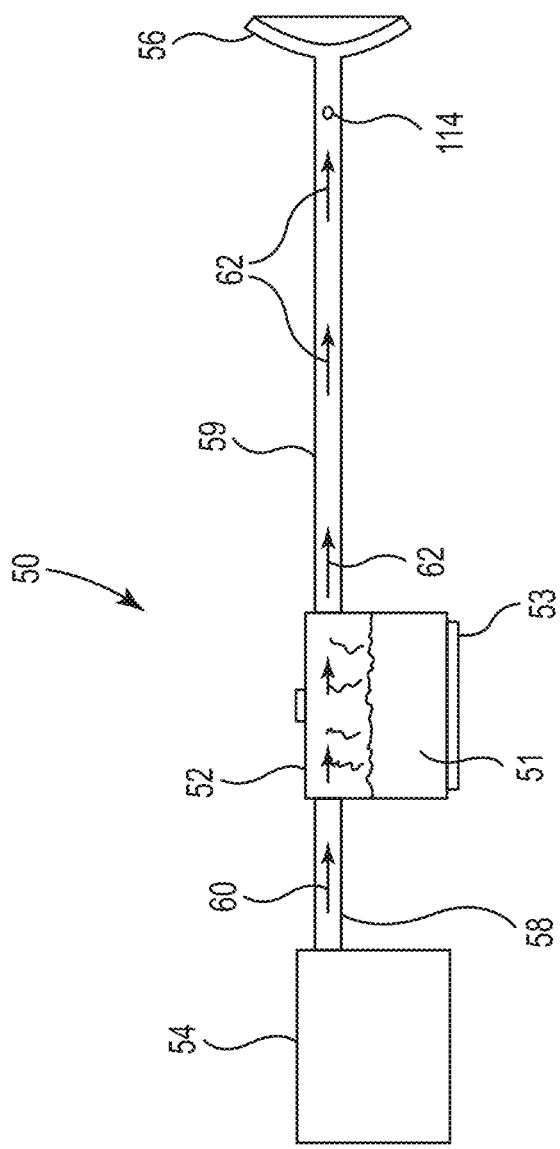
FIG. 1 is a diagrammatic illustration of a positive airway pressure (PAP) apparatus incorporating a conventional heated (e.g., water surface) humidifier.

The figures are rendered primarily for clarity and, as a result, are not necessarily drawn to scale. Moreover, various structure/components, including but not limited to fasteners, electrical components (wiring, cables, etc.), and the like may be shown diagrammatically or removed from some or all of the views to better illustrate aspects of the depicted embodiments, or where inclusion of such structure/components is not necessary to an understanding of the various exemplary embodiments described herein. The lack of illustration/description of such structure/components in a particular figure is, however, not to be interpreted as limiting the scope of the various embodiments in any way.

DETAILED DESCRIPTION OF EXEMPLARY EMBODIMENTS

In the following detailed description of illustrative embodiments, reference is made to the accompanying figures of the drawing which form a part hereof. It is to be understood that other embodiments, which may not be specifically described and/or illustrated herein, are also contemplated.

All headings provided herein are for the convenience of the reader and should not be used to limit the meaning of any text that follows the heading, unless so specified. Moreover, unless otherwise indicated, all numbers expressing quantities, and all terms expressing direction/orientation (e.g., vertical, horizontal, parallel, perpendicular, etc.) in the specification and claims are to be understood as being modified in all instances by the term "about."

Embodiments described herein are directed to positive airway pressure (PAP) apparatus and systems incorporating a humidifier, and to methods of adding humidity to gas provided by a PAP apparatus. Exemplary PAP systems, like those described herein, are adapted to modulate delivery of humidity in proportion to a rate of flow of pressurized gas produced by the PAP apparatus so that a generally constant level of humidity is provided to the user during an inspiration portion of each breath cycle. In other embodiments, the PAP apparatus may deliver added humidity to a portion of the flow of pressurized gas that reaches a user interface (attached to the user) during a portion of the breath cycle (e.g., during inspiration), and potentially reduce or even suspend providing the added humidity to another portion of the flow of pressurized gas that reaches the user interface during a second portion of the breath cycle (e.g., during expiration). As a result, some embodiments using humidifiers like those described herein may provide the user with a generally constant level of humidity during inspiration, regardless of changes in a rate of the flow of pressurized gas, over the course of the treatment period. Moreover, in some embodiments, the PAP apparatus (e.g., humidifier) may vaporize only a volume of water needed to provide a desired target humidity level at the user interface primarily during inspiration. In still other embodiments, the introduction of added humidity to the flow of pressurized gas may occur remotely from the user interface, but be timed to reach the user interface at the expected or predicted time of inspiration.

As further described below, exemplary humidifiers as described herein may humidify gas within the PAP apparatus by utilizing a vaporizing device that vaporizes water when the device is electrically powered (e.g., when electrical power is provided to a moisture transfer or vaporizing element of the vaporizing device) and reduces or terminates vaporization when power is correspondingly reduced or terminated. Moreover, a rate of vaporization and the volume of water per unit of time that is vaporized may be dependent upon the level of power provided to the device such that modulating power to the vaporizing device may proportionally modulate the rate of vapor produced.

By providing added humidity proportional to the flow of pressurized gas during at least a portion of the breath cycle, the volume of liquid (e.g., water) required, as well as the energy necessary to convert the liquid to vapor, may be less than that required for conventional (e.g., heated water surface humidifiers such as system 50 of FIG. 1) PAP humidifiers. The size of the humidifier reservoir, and the power required to convert the liquid to vapor, may be correspondingly reduced. Moreover, embodiments of the present disclosure may provide increased humidification levels using reservoirs of similar size to conventional heated water surface humidifiers.

As used herein, the terms "PAP," "PAP system," "PAP apparatus," etc. refer to positive airway pressure treatment systems for use in treating a variety of respiratory conditions including but not limited to obstructive sleep apnea (OSA), asthma, bronchitis, chronic obstructive pulmonary disease (COPD), pneumonia, congestive heart failure, and snoring. Such PAP systems may be adapted for use on both stationary and ambulatory users, including applications for non-invasively ventilating patients having restrictive lung disease or hypoventilation syndromes using bi-level positive airway pressure (Bi-PAP) therapy, or adaptive servo-ventilation for the treatment of complex sleep apnea. PAP systems may not include, and may be differentiated from, critical care ventilation, wherein the upper airway is completely bypassed and ventilation occurs via a tracheostomy. In the case of critical care ventilation, relative humidity levels at or near 100% (with air temperatures at or near body temperature) are common, as compared to lower relative humidity (e.g., 70-95%) typically provided during PAP therapy (with air temperatures at, near, or somewhat above room temperature).

As used herein, the terms "breath cycle" (and "breathing cycle") refer to a respiratory cycle of a user that includes one inspiration (the "inspiratory phase") followed by one expiration (the "expiratory phase"). The time it takes to complete one breath cycle is referred to herein as a "breath period." While breath cycles may vary extensively depending on the user and the user's respiratory condition, a flow-versus-time plot of a typical breath cycle may have a generally sinusoidal shape, possibly with different inspiratory and expiratory periods or ratios ("I:E ratios"), the latter which typically range from 1:1 to 1:2. However, significant deviations from this range can occur, e.g., with patients having respiratory diseases.

It is noted that the terms "comprises" and variations thereof do not have a limiting meaning where these terms appear in the accompanying description and claims. Further, "a," "an," "the," "at least one," and "one or more" are used interchangeably herein. Moreover, relative terms such as "left," "right," "front," "fore," "forward," "rear," "aft," "rearward," "top," "bottom," "side," "upper," "lower," "above," "below," "horizontal," "vertical," and the like may be used herein and, if so, are from the perspective observed in the particular figure. These terms are used only to simplify the description, however, and not to limit its scope in any way.

FIG. 1 illustrates a conventional PAP system 50 with a humidifier having a heated reservoir 52 positioned between a PAP blower 54 and a user interface or mask 56. The humidifier may include a heating element 53 operable to heat a volume of water 51 contained in the reservoir 52 to a point where the water evaporates. A rigid or flexible conduit 58 may connect an output of the blower 54 to an inlet of the reservoir 52, while a hose 59 typically connects an outlet of the reservoir to an inlet of the mask 56. The hose 59 (or the mask 56) may include an exhaust vent 114. A flow of pressurized gas 60 generated by the blower 54 may pass through the humidifier reservoir 52, wherein evaporating moisture becomes entrained therein to produce a flow of humidified gas 62, which is ultimately provided to the mask 56 by the hose 59.

In a configuration like that of FIG. 1, a relatively large volume of water having a correspondingly large surface area is typically provided to permit the pressurized flow of gas 60 produced by the blower 54 to gather the desired vapor content as it passes over the water in the reservoir 52 before travelling to the mask 56. While effective, the large volume of water, and the energy required to heat such a volume, may result in some inefficiency (e.g., elevated water consumption and power usage). Moreover, systems like system 50 generally have a relatively slow response time (i.e., the time required to change the reservoir temperature). Accordingly, controlling the vapor content of the flow of humidified gas 62 during system operation may be limited based upon how quickly the reservoir can be heated or cooled. As a result, humidification outside of the desired range could occur during at least a portion of the treatment period. For example, the system 50 may provide less that desired humidity levels when PAP pressure and/or flow rate are high. Additionally, such systems may result in increased flow resistance due to a circuitous airflow path (not shown) used to route the flow of pressurized gas over the expansive water surface. Such an airflow path may be of benefit, however, to minimize the chance of water leaking, e.g., back into the blower 54 or down the hose 59 to the user.

Figure 2:
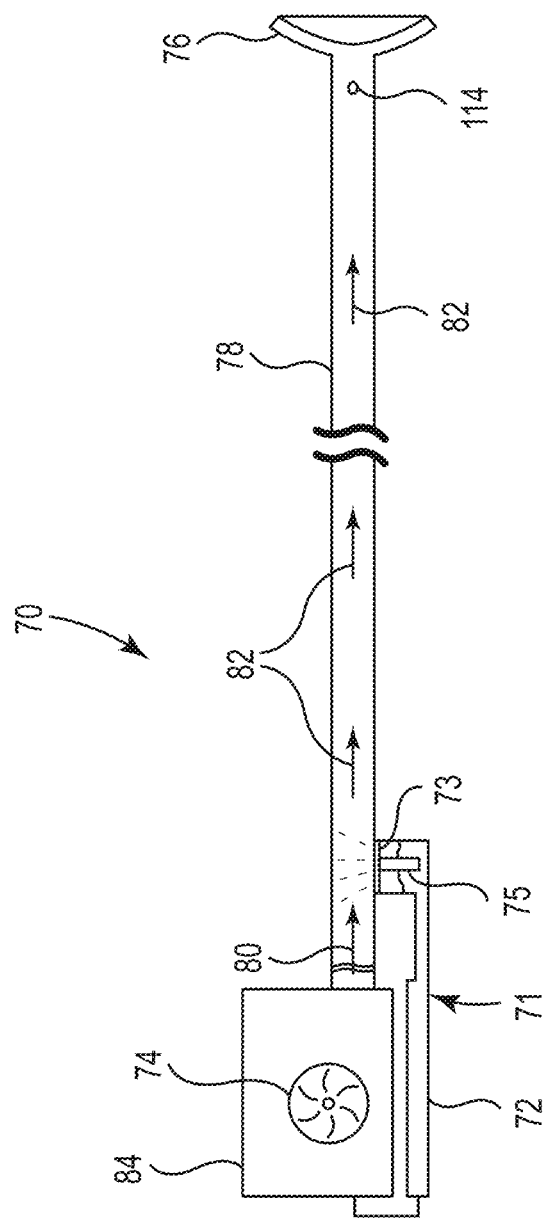
FIG. 2 is a diagrammatic illustration of an exemplary PAP apparatus incorporating a humidification system in accordance with one embodiment of this disclosure.

With reference to the figures of the drawing, wherein like reference numerals designate like parts and assemblies throughout the several views, an exemplary embodiment of a PAP apparatus 70 in accordance with one embodiment of this disclosure may be configured as diagrammatically represented in FIG. 2. As shown in this view, the PAP apparatus 70 may include a flow generator having a flow generator housing 84 containing a blower 74, a user interface (mask 76), and a delivery tube 78 positioned between the flow generator (blower) and the user interface and operatively connecting the blower/housing to the mask. The flow generator (e.g., blower 74) may be adapted to produce a flow of pressurized gas (e.g., at a variable flow rate and at a constant pressure regardless of the flow rate), wherein the delivery tube 78 is operable to transport (communicate) the flow of pressurized gas produced by the blower from an outlet of the blower 74/housing 84 to an inlet of the user interface. Once again, the delivery tube 78 or the mask 76 may include a vent 114.

The apparatus 70 may include a humidifier having a moisture transfer element capable of rapidly initiating and terminating moisture delivery to the flow of pressurized gas (e.g., delivering moisture during a first portion of a breath cycle and reducing or suspending delivery of moisture during a second portion of the same breath cycle). In the embodiments described and illustrated herein, the moisture transfer element may be configured as a capillary force vaporizer (CFV) 73. The CFV 73 may be configured to introduce/add humidity to a flow of pressurized gas 80 produced by the blower 74 to create a flow of pressurized gas with added humidity 82 for delivery to the mask 76. The CFV 73 may be part of a humidification subsystem 71 of the apparatus 70 that also includes a reservoir 72 and a water conveying device 75 (e.g., a wick or small tube (with or without a water pump)) operable to transport water from the reservoir to the CFV.

In one embodiment, some or all of the humidification subsystem 71 may be physically separate from the blower 74/housing 84 as shown in FIG. 2 (although electrical interconnections may be provided). In other embodiments, as shown in the partial view of the apparatus 70 in FIG. 3, some or all of the humidification subsystem 71 may be contained within the same housing (e.g., flow generator housing 84) that encloses the blower 74. The latter configuration may permit for a more compact design, while the former may be more conducive to retrofitting existing PAP apparatus. The embodiment of FIG. 3 may also provide advantages such as: reduced cost; smaller, unitary housing; integrated electronics (e.g., single printed circuit board (PCB)); elimination of external interconnects; and a single power supply. While not illustrated in FIG. 3, other embodiments could separate the water reservoir 72 from the housing 84, e.g., to simplify refilling.

Figure 3:
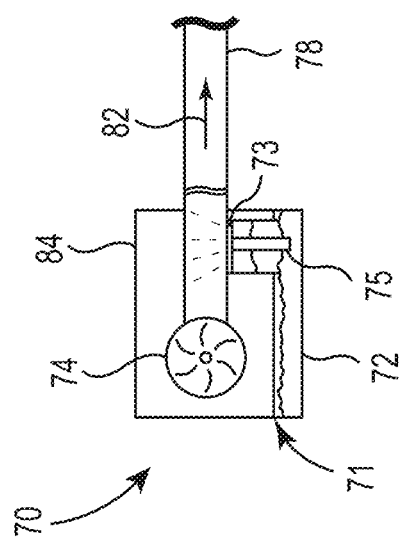
FIG. 3 is a diagrammatic, partial illustration of an exemplary PAP apparatus incorporating a humidification system in accordance with another embodiment.
Figure 4:
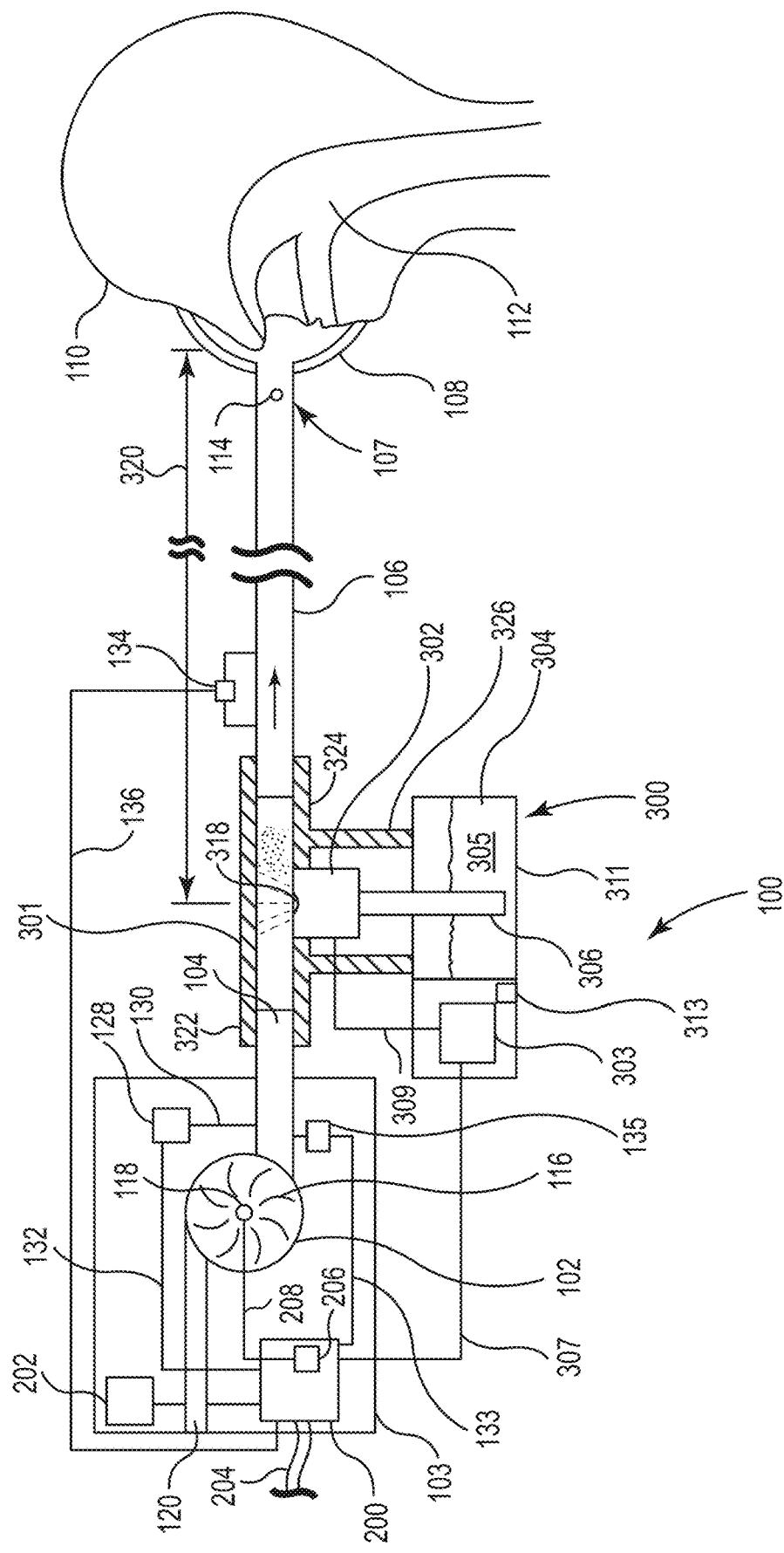
FIG. 4 is an enlarged diagrammatic view of a PAP apparatus having a humidification system in accordance with yet another embodiment.

With this general introduction, FIG. 4 illustrates an exemplary embodiment of a PAP system or apparatus 100 in accordance with another embodiment of this disclosure. The apparatus 100 may be similar in many respects to the apparatus 70 described above in FIGS. 2 and 3 (e.g., it may utilize a humidification subsystem incorporating a CFV).

The PAP apparatus 100 may include a flow generator or blower 102 having an outlet 104 that may be in communication with a first or proximal end of an elongate delivery hose or tube 106 positioned between the flow generator (e.g., blower 102) and a user interface or mask 108. In the illustrated embodiment, a T-shaped connector 301 (in cross-hatched section) may be located between the outlet 104 and the delivery tube 106 for reasons that will become apparent.

A second or distal end of the delivery tube 106 may be connected to an inlet of the user interface 108. The user interface 108 is illustrated generically, but is understood to include most any interface that seals effectively to a user 110 (e.g., about the user's face (nose and/or mouth) or within the user's nares) in such a way that a flow of pressurized gas delivered to the user interface may be communicated to an airway 112 of the user during treatment (e.g., during one or more breath cycles). For example, the user interface could be a face mask that covers one or both of the user's mouth and nose; a nares pillow seal; or any similar device or combination of such devices. For simplicity, the user interface may be referred to hereinafter as a "mask" without limitation.

As used herein, the term "gas" is understood to include most any gas or gas-vapor combination. For example, the gas provided by the blower 102 may include air, oxygen, water vapor or droplets, medicinal vapor or droplets, and combinations thereof. For simplicity of description, the terms "air," "fluid," and "gas" may be used interchangeably herein. "Pressurized gas," as used herein, refers to gas at a positive pressure relative to ambient pressure. "Blower," as used herein, refers to most any device or source capable of producing a flow of pressurized gas.

The delivery tube 106 and user interface (mask) 108 may together define a delivery conduit 107 forming a passage that transports or otherwise communicates the flow of pressurized gas from the outlet 104 of the blower 102 to the inlet of the mask and then to the airway 112 of the user 110. The delivery conduit, e.g., delivery tube 106 or mask 108, may include one or more exhaust vents 114. Such vents are known to provide what is referred to an "intentional leak." Intentional leak is provided to assist in purging carbon dioxide from the delivery conduit 107 during the expiration phase of each breath cycle. In one embodiment, one or more vents 114 may be included and provide the equivalent of a single, four millimeter (mm) opening (although other leak sized are certainly possible). In practice, the vent leak may vary widely (e.g., up to six mm opening) depending on mask type.

To provide the desired flow of pressurized gas within the delivery conduit 107, the blower 102 may be part of a flow generator having a flow generator or blower housing 103 forming a volute containing an impeller or fan 116. An electric motor 118, such as a brushless DC motor, may rotate the fan during use. As the fan rotates, it draws gas (e.g., ambient air) in via an inlet 120 of the blower 102/housing 103, where the gas is then compressed by the fan and expelled through the outlet 104. By controlling the rotational speed of the fan 116, the pressure of the gas within the delivery conduit 107 may be controlled to provide the desired treatment pressure to the user 110.

The apparatus 100 may further include a gas flow or PAP controller 200 that, among other tasks, may modulate or otherwise control a speed of the motor 118 (and, accordingly, a speed of the fan 116) to, for example, produce a variable flow rate at a constant pressure. The PAP controller 200 may, in one embodiment, include a microprocessor-based motor controller 206. All electrical components may be powered by either an onboard electrical power source or supply (e.g., a battery 202) or a remote power supply (AC or DC source) via an electric cord 204. The PAP controller 200 may electrically interconnect other components of the system 100 as further described herein.

The PAP controller 200 may be contained within the blower housing 103 as shown in FIG. 4. Alternatively, the PAP controller could be housed in a separate enclosure (not shown).

The PAP apparatus 100 may further include a pressure transducer 128. In one embodiment, the pressure transducer 128 is located within the housing 103. For example, in the illustrated embodiment, the pressure transducer 128 is located within the housing 103 and is connected at or near the outlet 104 (or, alternatively, connected at most any other point along the delivery conduit 107) via a pressure line or conduit 130. The pressure transducer 128 may produce an electrical signal proportional to the actual, measured pressure within the delivery conduit 107. The pressure signal may then be transmitted to the PAP controller 200 via an electrical signal line 132 as illustrated in FIG. 4. As further described below, the PAP controller 200 may compare the pressure signal to a commanded pressure and, via closed-loop control, modulate a commanded motor speed to the motor 118 via a command line 208 from the motor controller 206. As a result, the apparatus 100 may maintain a desired pressure in the delivery tube 106/mask 108 regardless of anticipated variations in flow.

In other embodiments, additional sensors, e.g., a pneumotachometer 134 (e.g., a differential pressure transducer placed across a known restriction), may also be provided as shown in FIG. 4 (the pneumotachometer may be placed most anywhere in the apparatus 100 (e.g., anywhere between the air inlet 120 and the mask 108). The pneumotachometer 134 may provide the PAP controller 200 with an electrical signal proportional to the instantaneous flow within the delivery conduit 107 via a sense line 136. Other sensors 135, e.g., temperature, humidity, etc. may also be provided and electrically connect to the PAP controller 200 as indicated (see e.g., line 133).

While described as a pneumotachometer, other devices and/or methods for measuring or estimating air flow may also be used. For example, other embodiments may analyze a speed of the motor 118 or the voltage, current, or power draw of the motor.

The exemplary apparatus 100 may, in one embodiment, further include a humidifier subsystem ("humidifier 300") as diagrammatically illustrated in FIG. 4. The humidifier 300 may include the vaporizing device (which may be a CFV 302), a water source or reservoir 304, and a water conveying device 306 (e.g., a wick or small tube (again, with or without a pump)) connecting the water source 304 with the vaporizing device. The humidifier (i.e., the vaporizing device), embodiments of which are described in more detail below, may be positioned proximate the blower, e.g., between the blower 102 and the delivery tube 106 (or elsewhere along the delivery conduit 107), such that an outlet 318 of the humidifier (e.g., of the vaporizing device) is in communication with the flow of pressurized gas produced by the blower 102. While the vaporizing device could be located at most any position along the delivery tube 106, the mask 108 (either before or after the port 114), or even at or within the housing 103 (as further described below), it is, in the illustrated embodiment, positioned between the blower and the delivery tube, e.g., within the T-shaped connector 301. The connector 301 may include a first leg 322 connected to the outlet 104 of the blower 102/housing 103, and a second leg 324 connected to the delivery tube 106 as shown in FIG. 4. A base leg 326 of the T-shaped connector 301 may then receive and support the vaporizing device. In one embodiment, a peripheral edge of the vaporizing device (e.g., CFV 302) is sealed against an inner surface of the connector 301 such that the flow of pressurized gas does not escape through the T-shaped connector. In other embodiments, a pressure equalization port may be positioned between the delivery conduit 107 and the reservoir 304 to equalize a pressure therebetween.

When configured as described above, the apparatus 100 places the vaporizing device in communication with the flow of pressurized gas and at or near the outlet 104 of the blower 102/housing 103. Such a configuration may simplify the apparatus 100 by shortening fluid connections between the water reservoir 304 and the vaporizing device. For example, the water source 304 may be located adjacent the blower housing 103 as indicated in FIGS. 2 and 4 (or alternatively, within the PAP housing 103 as shown in FIG. 3).

In one embodiment, water 305 contained within the water reservoir 304 may be conveyed, via wicking or capillary action, to the vaporizing device (e.g., CFV 302) by the water conveying device 306. While so illustrated, other embodiments may utilize a pump (fixed or variable displacement, peristaltic, etc.) connected to the water reservoir 304 and the vaporizing device to convey water from the former to the latter. In such a configuration, the pump may be activated (e.g., by a humidification controller 303) to deliver water, via a water line, to the vaporizing device. In some cases, the water conveying device 306 may simply be a short, small diameter capillary tube (without a pump). Water may then be conveyed by the tube via capillary force created by the vaporizing device, as well as capillary forces created by walls of the tube, or by gravity (depending on the position of the reservoir).

Conventional heated humidifiers (see, e.g., FIG. 1) operate by passing all of the PAP-generated gas over the relatively large surface area of water in a water reservoir. The entire reservoir of water is then heated to enhance the amount of water that evaporates into the gas stream. This continual heating of the water reservoir requires sustained power as it continuously humidifies the gas flowing through the tube 62 (regardless of flow rate of the gas), much of which escapes out the vent 114 rather than ultimately making its way to the airway of the user.

Unlike these conventional PAP humidifiers, the humidifier 300 (e.g., the vaporizing device) may, in one embodiment, be a CFV 302 such as the humidifier element used in the MyPUREMIST model CFV 100 personal humidification unit distributed by Vapore, LLC. of Concord, Calif., USA. Such CFV devices may convert water into vapor by providing a heating or vaporizing element (e.g., heated surface area) that converts liquid to vapor via both capillary force and phase transition. The effect is that vapor may be forcefully emitted from the outlet 318 of the vaporizing device 302 upon electrically energizing (heating of) the vaporizing device. As a result, the PAP apparatus 100 may be able to rapidly and reliably control the vapor output of the CFV throughout the breath cycle to provide the flow of pressurized gas with the desired target humidity level. That is, because of the responsive nature of the CFV 302, humidification of the flow of pressurized gas (to produce a flow of pressurized gas with added humidity) may be precisely controlled during individual breath cycles to ensure a constant (or near constant) level of humidity is provided to the user during inspiration (over the entire treatment period), even when parameters such as breath rate, breath flow, leak magnitude (intentional or unintentional), tidal volume, and/or pressure changes. Thus, the CFV 302 may require heating only the amount of water that is needed to provide a constant (or near constant) target humidity level to the flow of pressurized gas delivered to the user interface. In other embodiments, the CFV 302 may add humidity (to reach the desired target humidity level) to only those portions of the flow of pressurized gas that reach the user interface primarily during the inspiratory phase of each breath cycle. Accordingly, disadvantages associated with conventional humidifiers (e.g., heating of a large reservoir of water, delivering humidified gas to the user interface during the expiratory phase) may be avoided.

In the embodiment illustrated in FIG. 4, the humidifier 300 may include a humidifier housing 311 containing, among other components, the humidification controller 303 (also referred to herein as "controller"). The humidification controller 303 may be in communication with the vaporizing device (CFV 302) and a power source 313 such that it is operable to selectively deliver electrical power from the power source to the vaporizing device (e.g., during at least a portion of the breath cycle) via a power line 309. The humidifier 300 may include the separate power source 313 as shown to provide electrical power to the vaporizing device and to other components of the humidifier, or the humidifier may draw its power from the power source (e.g., battery 202 or source connected to cord 204) associated with the housing 103. The humidification controller 303 may also be electrically connected to the PAP controller 200 (e.g., via communication line 307) so that signals and other information regarding breath parameters (e.g., gas pressure, flow rate, and inspiration/expiration parameters) and humidification data, may be conveyed to/from the humidification controller. In other embodiments, some or all aspects of the humidification controller 303 and the PAP controller 200 may be incorporated into a single controller module (as could be the case with the system illustrated in FIG. 3). Accordingly, as used herein, the term "controller" may be understood to include either or both of the PAP controller and the humidification controller.

The humidification controller 303 and/or the PAP controller 200 may analyze data to determine various parameters associated with PAP operation. For example, breath rate, tidal volume, intentional leak flow, gas flow, mask leak flow, inspiratory/expiratory transitions, predictions regarding onset and/or duration of inspiratory phases of subsequent (future) breath cycles, algorithm functional constants and/or lookup tables, vaporizing device operating parameters (some of which are described in more detail below), among others, may all be analyzed and/or determined by the humidification controller 303 and/or the PAP controller 200. Still yet other parameters regarding operation of the PAP apparatus 100 (or PAP apparatus 70), e.g., volume (e.g., length and diameter) of the delivery tube 106, mask intentional leak, mask dead space, and desired humidification level may be user-provided, e.g., via a control panel or the like located on the housing 103 and/or the humidifier housing 311. Some of these parameters may be explicitly entered, while others may be selected from component classifications. For example, instead of entering explicit dimensions for the hose 106 and/or mask 108, the user may only be required to select a hose or mask part number or descriptor (e.g., "A,", "B," or "C"). The controller 200 (or 303) may then automatically determine intentional leak, hose volume, and other parameters.

The CFV 302 may respond quickly to commands from the controller 303 (or the controller 200). As a result, exemplary vaporizing devices (e.g., CFV 302) may be able to modulate vapor delivery to the flow of pressurized gas to provide, in one embodiment, the flow of pressurized gas with a generally constant level of humidity (e.g., a continuous modulation humidification mode) regardless of changes in rate of the flow of the pressurized gas. Moreover, in other embodiments, the apparatus (e.g., vaporizing device) may be able to reduce or even suspend vapor delivery (e.g., a discontinuous humidification mode) to a portion of the flow of pressurized gas (e.g., the portion that is present at the user interface during the expiratory phase of the breath cycle) by reducing or suspending electrical power to the vaporizing device, and then resume vapor delivery to another portion of the flow of pressurized gas (the portion that is present at the user interface during the inspiratory phase).

In either the continuous or discontinuous humidification mode, the total water and power required over the treatment period to provide the desired humidity level to the user during the inspiratory phase of each breath cycle (the "target humidity level") could be reduced as compared to conventional PAP humidification. In fact, it is contemplated that some embodiments of the PAP systems described herein (e.g., apparatus 70, 100, and 400) could provide the target humidity level to the user (at least during the inspiratory phase of each breath cycle) over the course of a typical treatment period (e.g., 8-10 hours) while using a smaller water reservoir and less power (as compared to conventional PAP humidifiers).

As an example, a conventional water surface humidifier may have a reservoir size of 300-500 cubic centimeters (cc) and require 60-500 watts (on average) to adequately deliver a desired humidity level (e.g., up to 95% relative humidity) over a treatment period of 8 hours. It is believed that a PAP apparatus like the apparatus 100 of FIG. 4 (or the apparatus 70 and 400 described herein) having a humidifier like the humidifier 300 (or humidifier 600 described below) could provide the same or similar target humidity level to the user during the user's inspiratory phase for the same treatment period of 8 hours using a reservoir size of 150-300 cc with power of 15-45 watts (on average). As a result, a smaller, more water- and energy-efficient PAP apparatus may result. Of course, actual performance of this or any other humidifier could vary, perhaps significantly, based upon a variety of factors including but not limited to: system pressure; tidal volume; minute volume; breath rate; flow rate; intentional leak; unintentional leak; desired humidity; and ambient temperature/humidity. For extreme conditions of high pressure (greater than 16 cm water), high intentional leak (e.g., as may be the case with a full face mask), and large unintentional leaks, systems like the system 100 (and the systems 70 and 400 described herein) could potentially provide higher humidity levels than that typically offered by traditional heated humidifiers. Of course, to provide such humidity levels, higher CFV power levels and water volumes may be needed.

While identified herein as a CFV 302, humidifiers having other types of moisture transfer elements now known or later developed that may provide similar performance/response are also contemplated.

Figure 5:
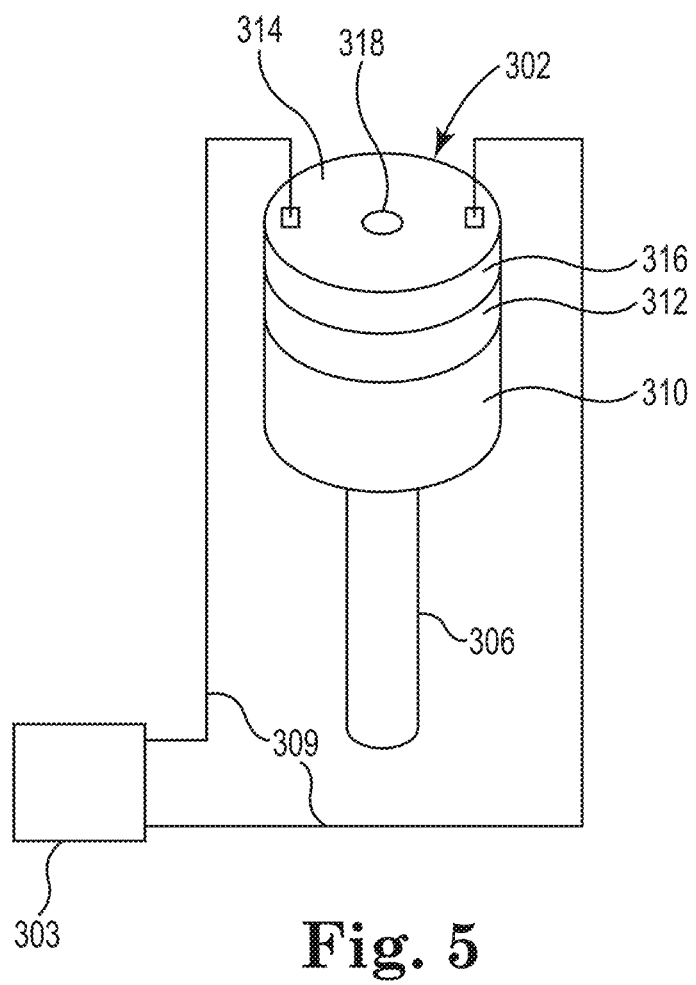
FIG. 5 is an enlarged view of a vaporizing device in accordance with one exemplary embodiment.

As shown in FIG. 5, the exemplary CFV 302 may form a vaporizing element that is an assembly of multiple layers of different porosity. For example, the CFV 302 may include a porous member that, in one embodiment, includes an insulating layer 310 and a vaporizing element 312. The porous member may be placed in contact with a heating/ejection layer 316. The heating layer may include a heater or heating element (powered by the power line 309) and a heat exchanger 314. The heating/ejecting layer 316 may include an outlet or opening 318 adapted to emit pressurized vapor (e.g., into the flow of pressurized gas within the delivery conduit 107) from vapor that collects in channels formed beneath the surface of the heating/ejecting layer. Water may be conveyed to the insulating layer 310 by the water conveying device 306 or via other mechanisms (e.g., gravity). For more information regarding exemplary CFV constructions, see, e.g., U.S. Pat. App. Pub. No. 2010-0142934 and U.S. Pat. Nos. 6,634,864 and 7,942,644.

By delivering power (i.e., electrical current) to the heating/ejecting layer 316, the temperature of the CFV 302 may be elevated rapidly, permitting vapor to be almost instantaneously produced and forcefully emitted by the heating/ejecting layer 316 (via the opening 318) into the flow of pressurized gas. Moreover, assuming that adequate liquid is available to the vaporizing element 312, the volume of water vapor produced by the CFV 302 may be directly proportional to the power delivered to the CFV. As a result, output of the CFV 302 may be modulated (by modulating electrical power to the CFV) to accommodate variations in flow during the breath cycle.

Figure 6:
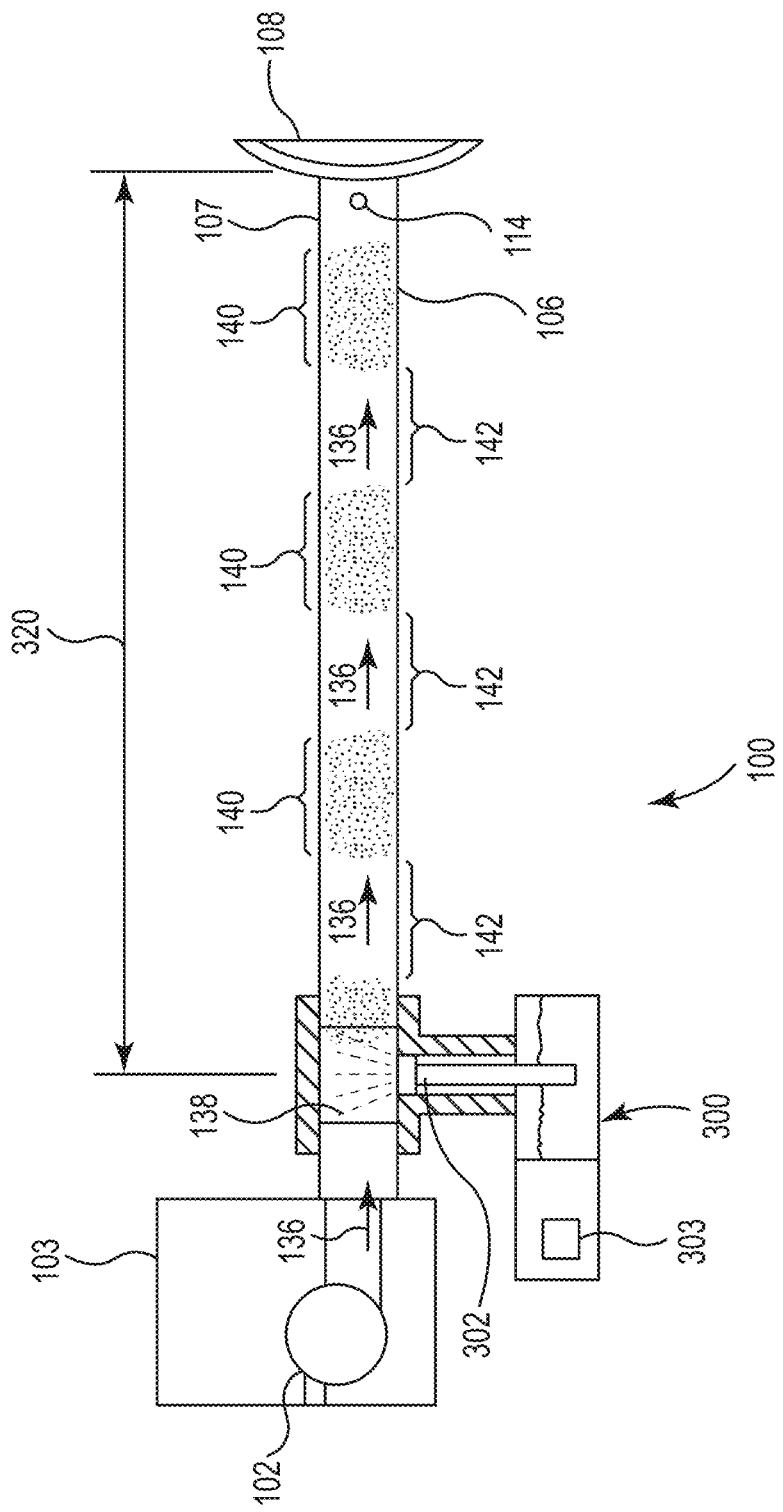
FIG. 6 is a diagrammatic section view of a delivery tube or conduit of the exemplary apparatus of FIG. 4 illustrating pulses or intervals of added humidity being provided to a flow of pressurized gas provided by the apparatus.

In some embodiments, the controller (e.g., controller 303 or controller 200) may be configured to simply monitor a rate of the flow of pressurized gas and automatically modulate the electrical power to the CFV 302 during the breath cycle. This process may modulate the amount of water vapor added in proportion to the flow of pressurized gas to maintain a generally constant target humidity level in the flow of pressurized gas (even as the flow of pressurized gas changes) during the breath cycle and over the treatment period. In other embodiments, the controller (303 and/or 200) may further analyze current or previous breath cycles to predict future breath/humidification needs, and command the CFV to provide added humidity primarily to those portions (the "inspiration portions") of the flow of pressurized gas that will reach the user interface 108 at or near the onset of the inspiratory phase of each breath cycle. In the case of this pulsed or discontinuous humidification mode of the CFV 302, the system may again provide a generally constant level of humidity to the patient during the inspiratory phases even as the flow of the pressurized gas changes over the course of inspiration. FIG. 6 may illustrate exemplary operation of this discontinuous humidification mode. Of course, in some embodiments, the CFV 302, under command of the humidification controller 303, may temporarily provide a higher humidity level (e.g., during peak gas flows and/or during high levels of inspiration). However, in such cases, the system 100 may maintain a general constant average humidity level for each breath cycle.

FIG. 6 diagrammatically illustrates a section view of the PAP apparatus 100 (similar to the PAP apparatus 70 and 400 described elsewhere herein) during operation, e.g., using the humidifier 300 of FIG. 4. As shown in this view, the delivery conduit 107 (e.g., the delivery tube 106) may route the flow of pressurized gas 136 generated by the blower 102 to the user interface 108. The CFV 302 may, at least in one embodiment, periodically eject water vapor 138 into the flow of pressurized gas 136, whereby the vapor becomes entrained therein to produce periodic, discrete pulses or flows of pressurized gas with added humidity 140 carried within the delivery conduit 107 as represented by stippled sections in FIG. 6. Because the vapor produced by the CFV 302 is responsive to changes in electrical power provided to the heating/ejecting layer 316 (see FIG. 5), the power delivered to the CFV 302 to produce each of the flows of pressurized gas with added humidity 140 may, in one embodiment, be modulated to maintain relatively constant humidity as the rate of flow of the pressurized gas increases/decreases. Such changes in rate of flow may occur, for example, during normal inspiration and expiration, when PAP pressure and/or flow rates change due to unintentional leaks and mask re-sealing (the latter which may occur during user movement), and in response to sleep disordered events (e.g., when using an Auto-PAP device).

Power to the CFV 302 may be reduced substantially or suspended altogether (in some embodiments) during a portion of the breath cycle to effectively reduce or even terminate the introduction of additional humidity into the flow of pressurized gas 136. As a result, the flow of pressurized gas may include the pulses or flows of the pressurized gas with added humidity 140 separated by periods of the flow of pressurized gas 142 that are non-humidified or "dry" as represented in FIG. 6. As used herein, the terms "non-humidified" or "dry" may be used to describe pressurized gas that lacks additional moisture intentionally provided by the CFV 302. However, those of skill in the art will appreciate that this non-humidified or dry gas may include some vapor content based upon the ambient gas from which the blower draws, or from residual moisture in the tube 106 or from the CFV 302, the latter resulting from a potentially less-than-instantaneous on/off response of the CFV to application of electrical power.

By applying principles in accordance with embodiments as described herein, the pulses or flows of pressurized gas with added humidity 140 may be timed to be delivered to the user interface 108 primarily during the inspiratory phase of each breath cycle. That is to say, water vapor may be provided by the CFV 302 to the inspiration portions of the flow of pressurized gas (to produce the flows of pressurized gas with added humidity) that are timed to reach the user interface during the inspiratory phase of each breath cycle. Conversely, the flows of non-humidified gas 142 may reach the user interface primarily during the expiratory phase of each breath cycle, or during pauses in breathing. Stated another way, the timing of the interval that produces the flow of pressurized gas with added humidity may be selected to ensure that the flow of pressurized gas with added humidity reaches the user interface 108 generally at or near an onset of the inspiratory phase of a current or subsequent (e.g., future) breath cycle and lasts for a duration of that inspiratory phase. Thus, added humidity to the flow of pressurized gas reaching the user during the expiratory phase may be reduced, minimized, or even avoided, thereby reducing the total volume of water required over the treatment period as well as reducing the power needed to provide the desired target humidity level to the user.

The timing of the delivery of the flows of pressurized gas with added humidity 140 may be complicated in some embodiments by the remote location of the humidifier (e.g., the vaporizing device (CFV) 302). That is, when the CFV 302 is positioned upstream of the user interface 108 by a distance 320, the flow of pressurized gas with added humidity 140 produced by the vaporizing device is delayed, after introduction, in reaching the user interface 108 (e.g., it lags behind the introduction of the added humidity). This delay is dependent on several factors including: the distance 320, the pressure of the flow of pressurized gas 136, tidal volume, and breath rate, as well as tube 106/mask 108 volume and intentional and unintentional leak flow. This delay could be at least partially alleviated by locating the CFV 302 closer to the user interface. However, moving the CFV 302 away from the housing 103 could result in a less compact design, e.g., power and water would need to extend to the CFV location.

Illustrative apparatus and methods like those described and illustrated herein may address this problem by accurately predicting when the onset of the next inspiratory phase will begin, and timing a start and duration of a power interval to the vaporizing device 302 to produce the pulses or flows of pressurized gas with added humidity 140. By accurately predicting inspiration and timing the power interval based upon that prediction, the apparatus 100 (or apparatus 70 and 400) may deliver the flows of pressurized gas with added humidity 140 to the user interface 108 beginning at the onset of the inspiratory phases and lasting for the duration of the inspiratory phases.

In one embodiment, injecting the humidity into the flow of pressurized gas may include injecting humidity into the flow of pressurized gas before the inspiratory phase of the target breath cycle, e.g., injecting the humidity during at least a portion of a breath cycle preceding the target breath cycle (e.g., the breath cycle for which the humidity is to be added). Moreover, each injection of humidity may be provided for the power interval duration (which is estimated or otherwise determined by the controller 303 or controller 200) to ensure that the added humidity is provided for most or all of the inspiratory phase of each breath cycle. Still further, the power delivered during the power interval may be modulated by the controller 303 to ensure delivery of a generally continuous level of humidity regardless of the flow of gas (i.e., the vapor emitted by the vaporizing device may be proportional to the flow within the conduit 107).

While not wishing to be limited to any specific embodiment, the power interval start time (also referred to herein as a power interval delay time) and duration, as well as how electrical power to the CFV will be modulated, may be determined based on one or more of: a pressure of the pressurized gas; total hose flow (which may include flow attributable to each of: intentional leak; unintentional leak; and breath cycle flow); a breath rate of the user; inspiratory tidal volume; expiratory volume; I:E ratio; inspiratory and expiratory flow dynamics (e.g., shape and amplitude of the flow curves); start and end times of both inspiration and expiration; time of peak flow during inspiration and expiration; power available to the vaporizing device, a volume of the delivery tube and the user interface between the outlet of the humidifier and the airway (which is a function of the distance 320); and a power-to-vaporization transfer function of the vaporizing device.

PAP apparatus and methods incorporating CFVs (e.g., apparatus 70, 100, and 400) may offer numerous benefits. For instance, by delivering vapor in proportion to the electrical power or current supplied to the CFV 302, humidity added by the CFV may be dynamically adjusted to meet the needs of a particular user, e.g., based upon actual breath needs. Moreover, as stated elsewhere herein, due to the responsiveness of the CFV 302, power to the CFV may be modulated during vaporization to minimize power and water usage while maintaining a relatively constant target humidity level based upon gas flow. In still other embodiments, power to the CFV may be entirely terminated during at least a portion of one or more breath cycles. As further described below, in embodiments that provide this discontinuous humidification, power delivery to and modulation of the CFV 302 may be initiated based upon a detected parameter of a breath (e.g., the onset of inspiration or expiration of a previous breath cycle, a peak inspiratory or expiratory flow, etc.).

Figure 7:
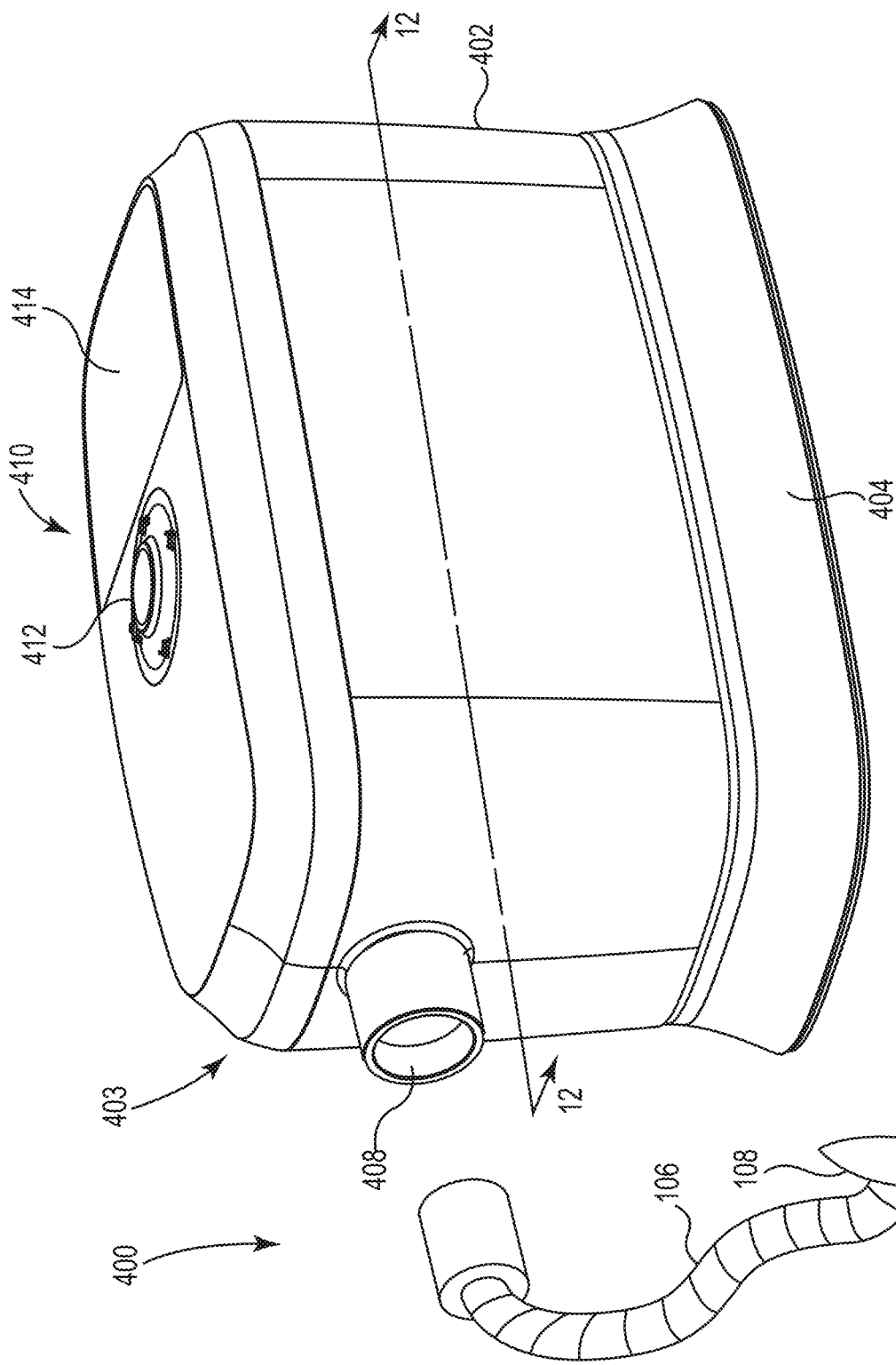
FIG. 7 is a front perspective view of a flow generator housing of a PAP apparatus in accordance with another embodiment of this disclosure.

FIGS. 7-14 illustrate an exemplary PAP apparatus 400 similar in many respects to the PAP apparatus 70 and 100 already described herein. The apparatus 400 may include a flow generator housing 403 that incorporates a humidifier subsystem, negating the need for separate humidifier housing. Aspects of the apparatus 400 (e.g., the housing 403) may be interchanged with, or combined with, aspects of the PAP apparatus 70 and 100 already described herein above. For example, the housing 403 may replace the housing 103 (and the humidifier 300) in the apparatus 100 of FIG. 4 such that the delivery tube 106 and user interface 108 would attach directly to an outlet 408 of the housing 403 as shown in FIG. 7.

Figure 8:
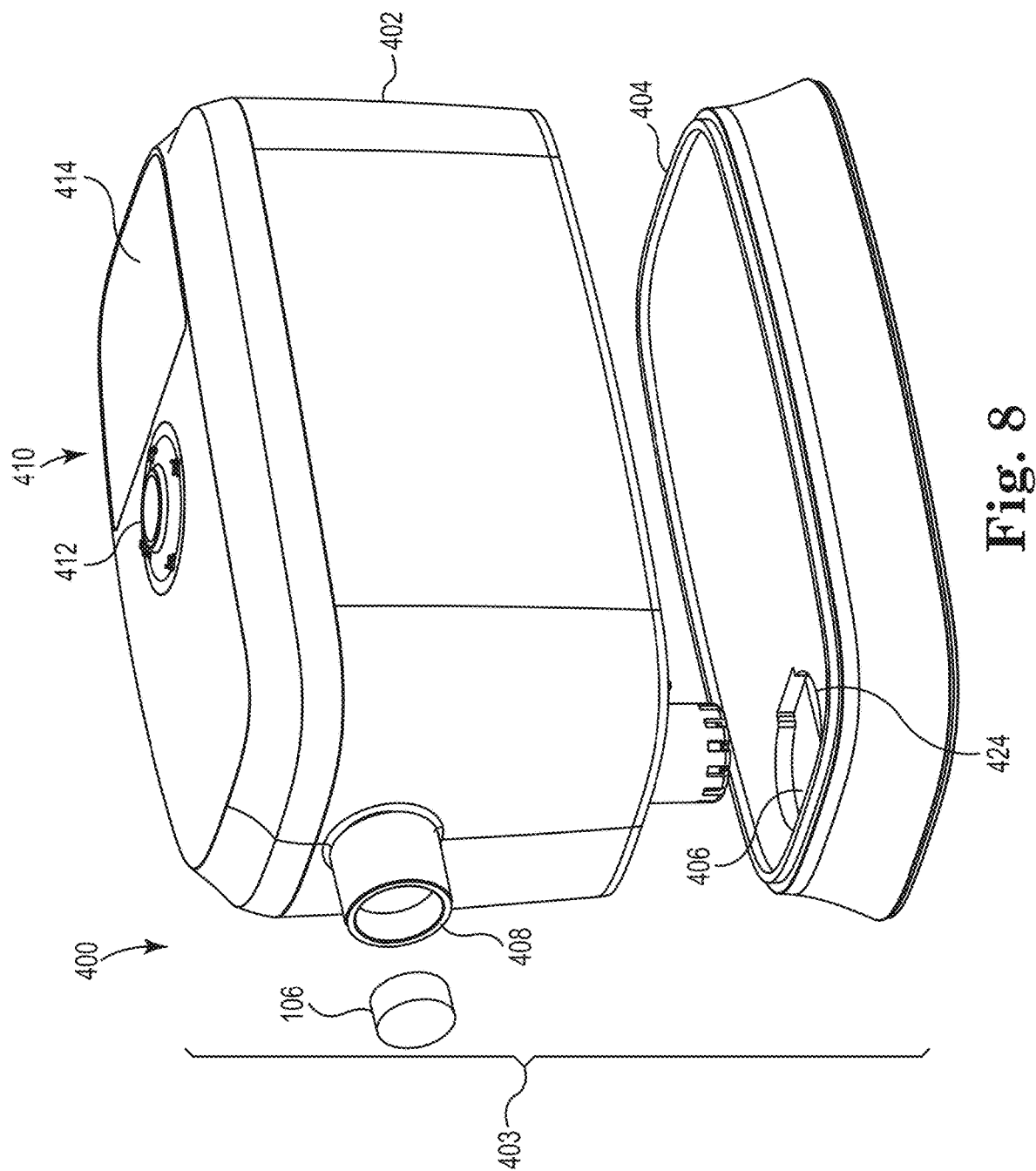
FIG. 8 is a front perspective view of the exemplary housing of FIG. 7 partially exploded.

As further shown in FIG. 7, the housing 403 may be defined by a body 402 and a base 404. In one embodiment, the base 404 may be separable from the body 402 as shown in FIG. 8 to provide access to a water reservoir 406 contained within the base. When assembled, the housing 403 may be adapted to rest upon a horizontal surface such as a tabletop or floor. The housing further defines the outlet 408 adapted to connect to the delivery tube 106 as already described herein.

The housing 400 may further define an Input/Output (I/O) or control interface 410 to permit user input and system feedback regarding operation of the apparatus 400. In one embodiment, the control interface includes an input device, e.g., directional joystick 412, and an output device, e.g., LCD screen 414. During operation, various operational parameters may be presented on the LCD screen, whereby the user may select and/or alter such parameters by manipulation of the input device. Of course, while shown as a joystick and LCD screen, such a configuration is not limiting. For example, a series of discrete knobs or switches, indicator lights, touchscreen interfaces, and the like could be used alternatively, or in addition, to the joystick and LCD screen shown. In yet other embodiments, the control interface 410 may be configured as a remote computer (e.g., smartphone) that communicates (via wired or wireless protocols) with the housing 403.

Figure 9:
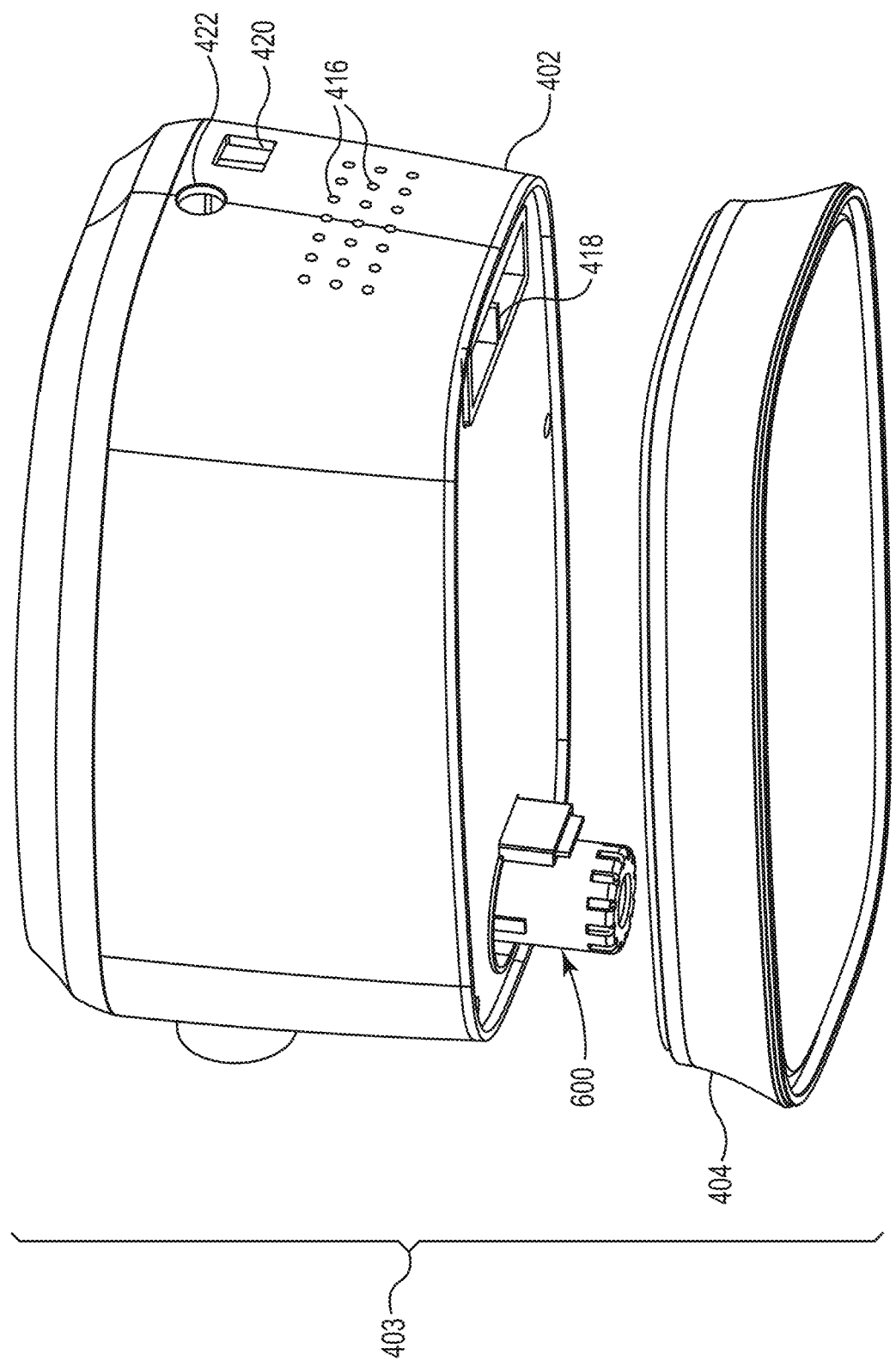
FIG. 9 is a rear perspective view of the exemplary housing of FIG. 7 partial exploded.
Figure 10:
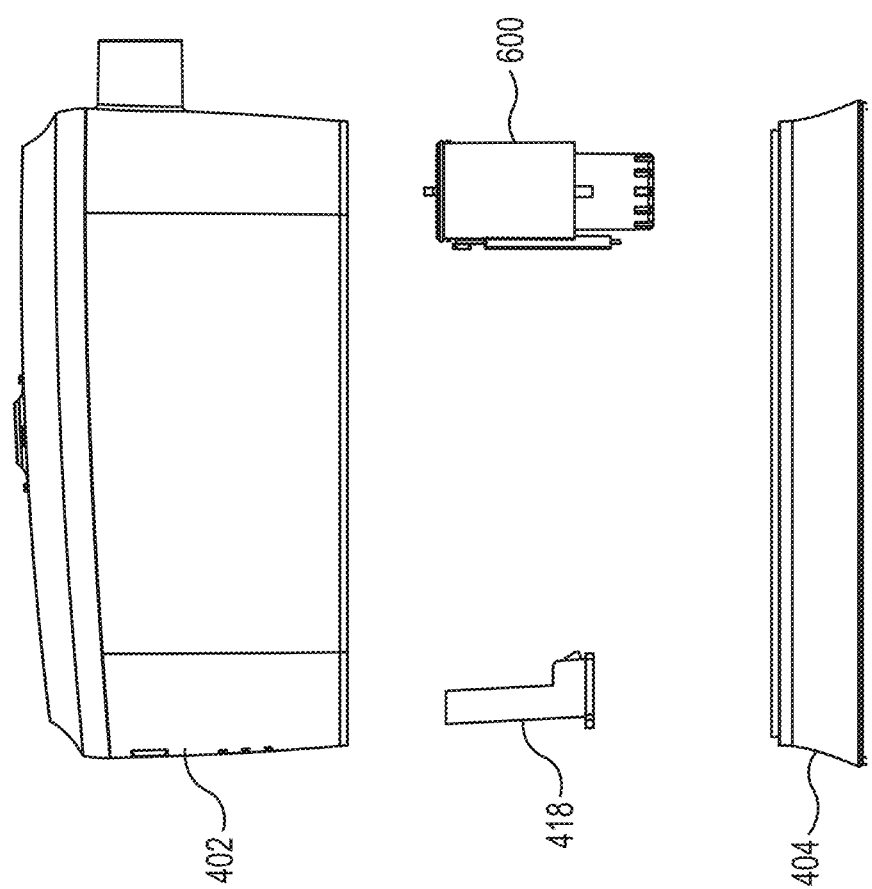
FIG. 10 is a side elevation view of the exemplary housing of FIG. 7 partially exploded.

FIG. 9 illustrates a rear perspective view of the housing 403 with the base 404 once again shown exploded from the body 402. As shown in this view, the housing may include one or more inlet passages 416 to permit a blower (not shown) contained within the housing 403 to draw ambient gas into the housing. To filter the ambient gas, an air filter cartridge 418 supporting air filter media may also be included. The rear side of the housing 403 as illustrated in FIG. 9 may also provide other features, e.g., on/off switch 420, a connector 422 for DC power connection, as well as other connectors (e.g., data port).

FIG. 9 also illustrates a lower portion of a humidifier 600. The humidifier 600 may extend into the water reservoir 406 (see FIG. 8) via an opening 424 formed in the base 404. The humidifier 600 is shown removed from the housing in FIG. 10. As shown in this view, separation of the base 404 from the body 402 may allow removal of the humidifier 600 as well as removal of the air filter cartridge 418, e.g., for maintenance.

Figure 11:
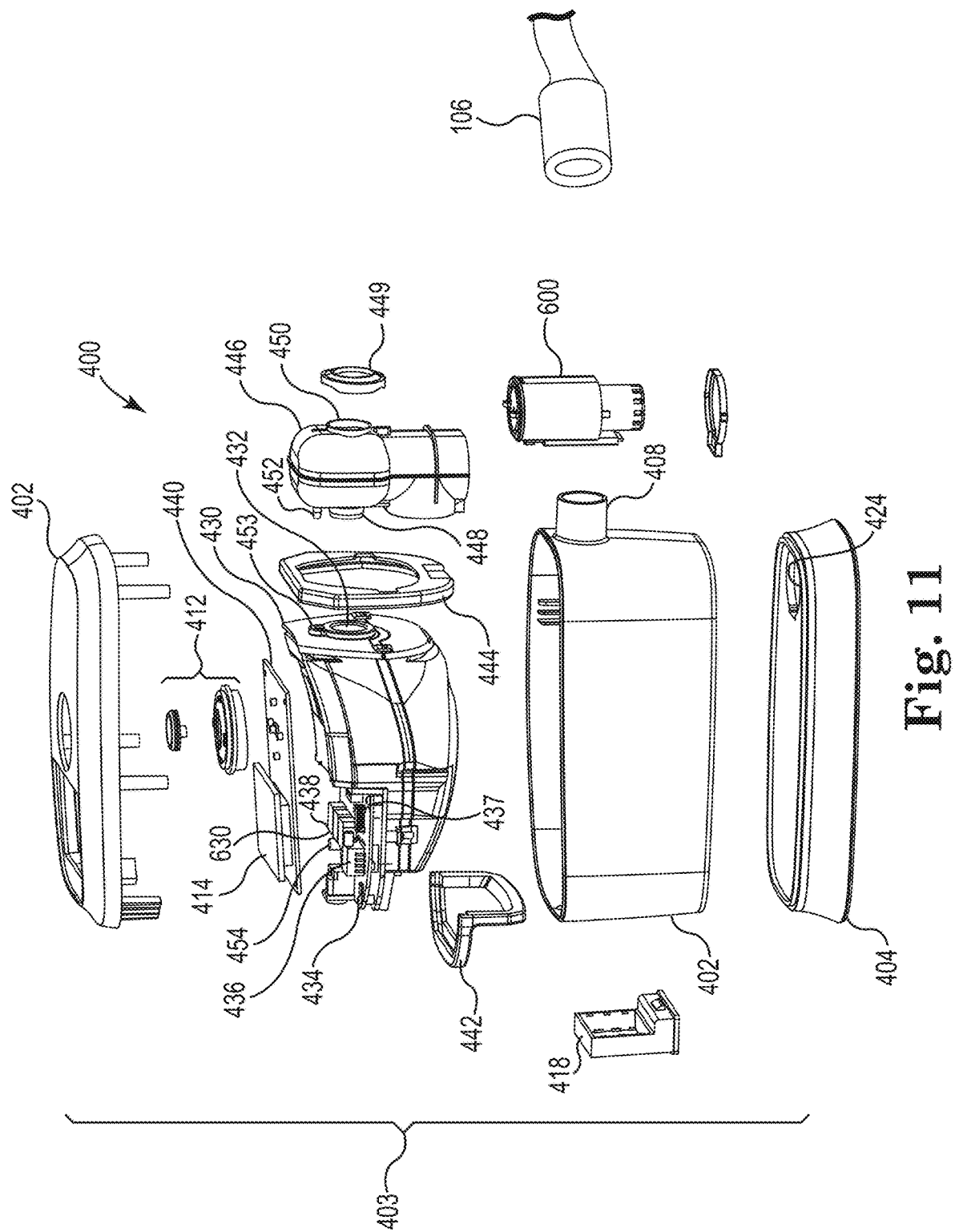
FIG. 11 is an exploded view of the exemplary housing of FIG. 7.

FIG. 11 is an exploded view of the exemplary housing 403. As shown in this view, the body 402 may form an open top container into which components of the apparatus 400 may install. The body 402 may further include a removable cap portion to cover the open top of the housing once assembled.

Within the housing 403, a blower assembly or blower 430 may be provided. The blower 430 may include an impeller 431 or fan powered by an electric motor 433 (see FIG. 12). When the impeller is rotated by the motor, it may draw ambient gas into a plenum (e.g., through the air filter cartridge 418) where the gas is then compressed and expelled outwardly through an outlet 432 of the blower as a flow of pressurized gas. By controlling the speed of the fan, pressure and rate of the flow of pressurized gas may be controlled. Like the other blowers described herein, the blower 430 may be able to maintain a sustained pressure even as the rate of flow of pressurized gas changes (e.g., during breathing).

Various electronics may also be included to provide real time control of the blower 430 and other aspects of the apparatus 400. In one embodiment, these electronics may be incorporated onto a printed circuit board (PCB) 434. The PCB may include a microprocessor 436, a PAP controller 437 (e.g., to control the blower 430), a humidity or humidification controller 630 (described in more detail below), and a memory unit 438.

The housing 403 may further contain an I/O board 440 that receives input from the joystick 412 and outputs information to the LCD screen 414. The I/O board 440 is in communication with the PCB 434 to permit bidirectional communication with the components of the PCB 434 and other components of the apparatus. The control interface 410 may allow various inputs including, for example, the target humidity level desired during operation. Such a humidity level may be referred to in relative terms, e.g., the control interface may provide settings 1-10, each corresponding to a successively higher target humidity level.

The housing 403 (e.g., the body 402) may also include various seals or covers to protect system components (e.g., a transparent cover may be provided over the LCD screen 414). The housing 403 may provide other seals to ensure that flow through the apparatus is contained. For example, an air filter cartridge seal 442 may be provided to ensure ambient air flows into the blower 430 and not to unintended areas of the housing 403.

A gasket 444 may be located at or near the blower outlet 432 between the blower 430 and a humidifier housing 446, the latter adapted to removably receive the humidifier 600 as further described below. The humidifier housing 446 may include an inlet 448 that communicates with the outlet 432 of the blower 430, and an outlet 450 that communicates with the outlet 408 of the housing 403. In one embodiment, a seal 449 may be provided between the outlet 450 and the outlet 408 to prevent pressurized gas from leaking into the housing 403.

The humidifier housing 446 may also include a pressure port 452 adapted to communicate with a conduit 453 on the blower 430. The conduit 453 may connect to a pressure sensor or transducer 454, e.g., located on the PCB 434.

Figure 12:
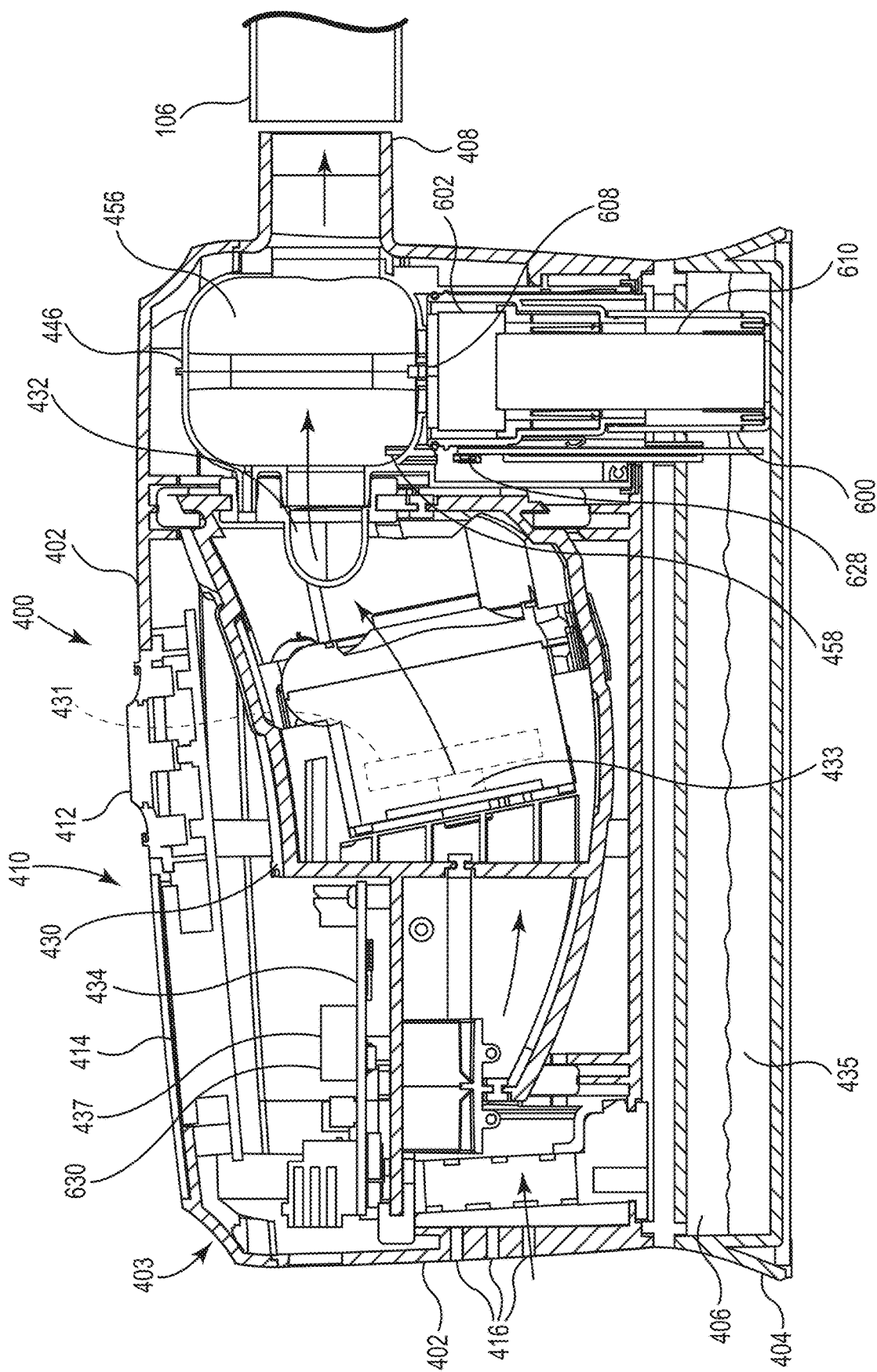
FIG. 12 is a section view taken along line 12-12 of FIG. 7.

FIG. 12 is a diagrammatic section view of the housing 403 as assembled. Note that some structure (e.g., electrical and fluid lines, fasteners, etc.) may be removed from this and other views to more clearly described aspects of the depicted embodiments. As shown in this view, the impeller 431 of the blower 430, whose speed is controlled by the motor 433 under control of the controller 437 on the PCB 434, may draw ambient gas into the housing 403 via the passages 416, compress the gas, and provide the flow of pressurized gas at the outlet 432 of the blower 430.

As will be further described below, the humidifier 600 may include a CFV 602 that vaporizes water 435 drawn from the reservoir 406 and emits the vapor into a humidification chamber 456 formed by the humidifier housing 446. In some embodiments, a sensor, e.g., a temperature and humidity sensor 458, may be provided. While the sensor 458 may be located most anywhere, it is, in one embodiment, located in the humidification chamber 456. The sensor 458 may provide a signal representative of the temperature and/or humidity level of ambient air at system startup. By providing the sensor 458 within the humidification chamber 456, the sensor may be used to monitor temperature and humidity during operation as well.

Figure 13:
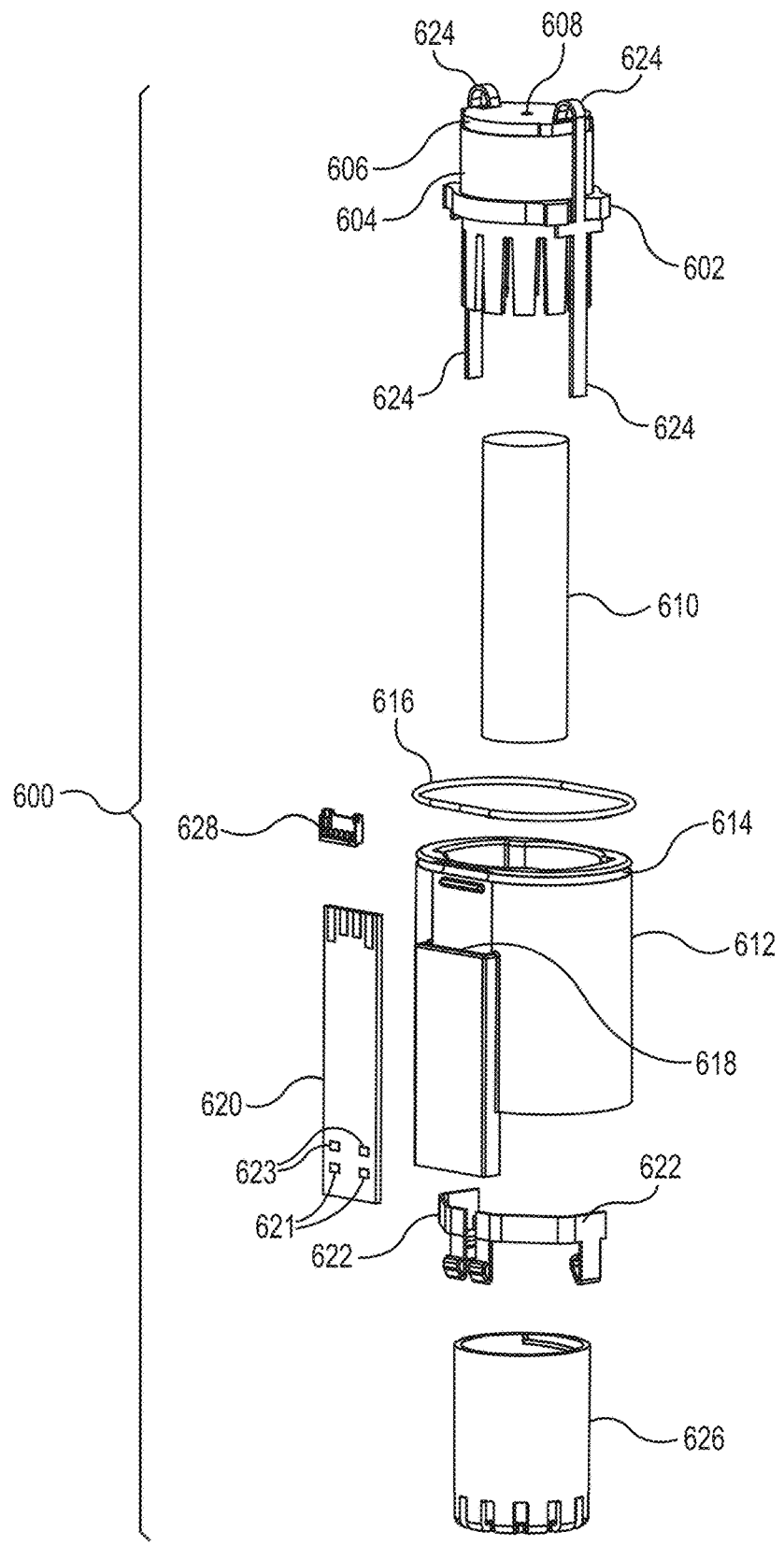
FIG. 13 is an exploded perspective view of a humidifier in accordance with one embodiment.

FIG. 13 is an exploded view of the exemplary humidifier 600. As shown in this view, the humidifier 600 may include a vaporizing device that, in one embodiment, is a CFV 602 similar to that already described herein. The CFV 602 may include a vaporizing element 604, which may be constructed of a sintered material, and a heating/ejection layer 606 defining an outlet or opening 608. A water conveying device 610, which may be configured as a small diameter tube or as a wicking material, may convey water 435 from the reservoir 406 (see FIG. 12) to the vaporizing element 604 via capillary action.

The humidifier 600 may further include a mounting sleeve 612 to hold the CFV 602. In one embodiment, the mounting sleeve 612 includes a groove 614 to hold a seal (e.g., O-ring 616), the latter adapted to seal the mounting sleeve relative to the humidifier housing 446/housing 403.

The mounting sleeve 612 may further include a receiver 618 for receiving and securing a PCB 620. Two contact members 622 may electrically couple contacts on the PCB to electrical leads 624 on the heating/ejection layer 606 of the CFV 602 when the humidifier 600 is fully assembled. A lower cap 626 may attach (e.g., via a screw thread) to the mounting sleeve 612. The lower cap 626 may protect elements of the humidifier 600, while also securing the water conveying device 610 within the humidifier. When correctly installed, the humidifier 600 may make electrical connection with the housing 403 (e.g., with the humidity controller 630 on the PCB 434) via an electrical connector 628 of the housing that engages associated contacts on the PCB 620.

Figure 14:
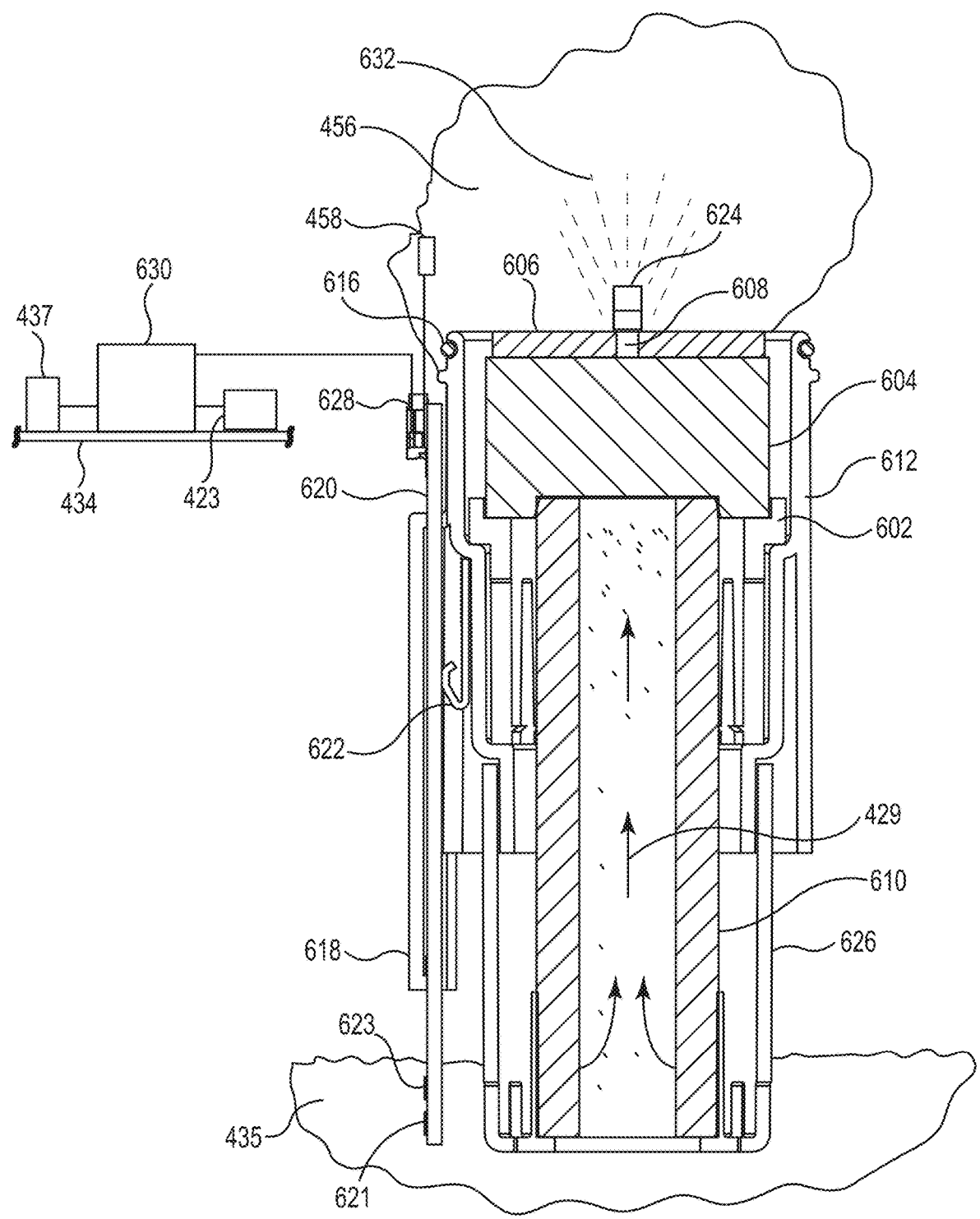
FIG. 14 is an assembled section view of the humidifier of FIG. 13.

FIG. 14 illustrates one embodiment of the humidifier 600 during use in a PAP housing, e.g., the housing 403. The humidity controller 630 may control delivery of electrical power from a DC power supply 423 (see FIG. 14, which could be a battery, or a DC transformer connected to an AC outlet). The humidity controller 630 may be in communication with the PAP controller 437 such that the water vapor output of the humidifier 600 may be correlated with the flow of pressurized gas delivered by the blower 430.

To generate vapor output, the humidity controller 630 may command a current to pass to the electrical leads 624 (see FIG. 13). This current causes a rapid increase in heat of the vaporizing element 604 and the heating/ejection layer 606. As these layers heat, water vapor 632 is produced and ejected through the opening 608 into the humidification chamber 456 (see also FIG. 12). Water vapor, as used herein, may include one or more of water vapor, liquid water droplets, mist, microdroplets, fog, and combinations of liquid water and water vapor.

As the vaporizing device vaporizes the water 435, more water is transferred to the vaporizing element 604 (as indicated by arrows 429 in FIG. 14) via the water conveying device 610 via wicking or capillary action. Of course, in other embodiments, a pump could be used to provide water to the vaporizing element 604. Thus, vaporization may continue as long as the water level of the reservoir 406 is of a level that ensures contact between the water conveying device 610 and the water. The housing 403, e.g., the PCB 620, could include a water level sensor 621 that would trigger an alarm and/or shut off the humidifier 600 when the water level was at or approaching empty. Moreover, some CFV constructions may operate most effectively with distilled water. As a result, some embodiments may include a water quality sensor 623 to detect impurities in the reservoir and respond, e.g., trigger an alarm, if threshold levels of impurities are detected.

Both the water level sensor 621 and the water quality sensor 623 may be electrically connected to the humidity controller 630 or flow controller 437, so that appropriate action may be taken in response to unacceptable water level and/or water quality. In some embodiments, both the water level detector 621 and the water quality detector 623 may utilize the same sensor (e.g., sensor contacts 621). For instance, water level and water quality may be assessed by monitoring the impedance between two exposed contacts 621 formed on the PCB 620. An intermittent current or voltage may be passed across the contacts (e.g., a 10 kHz symmetrical square wave), wherein a measured current or voltage may be detected when the contacts 621 are submerged. When water level drops below the contacts 621, continuity between the contacts breaks, indicating to the controller 630 (or 437) an out-of-water condition. In such an instance, the controller may sound an alarm or terminate power to the humidifier.

In addition to water level detection, the contacts 621 may also distinguish whether the water in the reservoir is distilled or whether it contains minerals that may potentially damage the CFV. For example, since distilled water has a very high but measureable impedance, and tap water has ions and/or minerals that provide a lower impedance, the controller 630 (or controller 437) may distinguish between distilled water and potentially damaging mineralized water. Based upon the determination that the water is not distilled, the controller 630 (or 437) may sound an alarm, provide an alert message on the display 414 (see FIG. 7), or even shut down the humidifier.

The water level sensor 621 and water quality sensor 623 may be positioned in locations other than those shown in the figures. For example, the sensors could be in contact with the water in the water conveying device 610 or at some other location within the reservoir 406. Moreover, other methods for detecting water level and quality may be utilized. For instance, piezo-electric sensors could be used. Such sensors may be located at positions similar to the sensors 621 and 623. Alternatively, water level and/or quality sensors may be configured as non-contacting sensors located above the water in the reservoir 604. For example, the water level sensor could be an ultrasonic sensor that emits an ultrasonic sound wave and measures transit time of pulses reflected from the water surface.

During operation, the apparatus (e.g., apparatus 400) may, upon initialization, determine a relative humidity level of the ambient air. This may be accomplished using the temperature and humidity sensor, e.g., sensor 458. The user may set a desired target humidity level, e.g., via interaction with the control interface 410. Based upon the relative humidity of the ambient air and its temperature and pressure, and upon the user-selected target humidity level of the flow of pressurized gas, the apparatus (e.g., PAP controller 437 or humidification controller 630) may determine how much water vapor should be added (per unit volume of gas) by the humidifier 600.

For example, if the apparatus determines that the ambient relative humidity is 40% and the ambient temperature is 23 degrees Celsius (° C.), the absolute humidity can be determined from known relationships (see, e.g., www.humidity-calculator.com) to be approximately 8.3 milligrams of water/liter of gas (mg water/L gas) for a given pressure. If the user wishes to achieve a target relative humidity of 80%, this would require an absolute humidity at the same temperature of 16.5 mg water/L gas. As a result, the apparatus (e.g., the controller 437 or controller 630) can determine that the humidifier 600 would need to add about 8.2 mg water/liter gas to achieve the desired target humidity level.

In one embodiment, the relationship between relative humidity and absolute humidity may be provided in a lookup table contained in memory (e.g., memory 438 of the PCB 434, see FIG. 11). In other embodiments, the relationship may be defined as shown in Equation 1 below:

$$AH = (0.0583 * e^{(0.0548*T)}) * RH \quad \text{(Equation 1)}$$

wherein AH is the absolute humidity in mg water/L gas; T is the temperature in degrees Celsius (° C.); and RH is relative humidity at temperature T expressed as a percentage. Based upon this equation, the apparatus 400 (e.g., the humidity controller 600 and/or the PAP controller 437) may calculate the vapor content need to achieve the target humidity level. As is evident from Equation 1 above, the relationship between AH and RH, for a given temperature, may be expressed linearly.

Accordingly, apparatus in accordance with embodiments as described herein (e.g., apparatus 70, 100, and 400) may calculate how much water vapor needs to be added per unit volume of gas flow to achieve the desired target humidity level. As stated above, the apparatus may subtract from these calculated humidity levels the moisture content already present in the ambient gas and provide only the difference as added humidity to the flow of pressurized gas.

The apparatus (e.g., apparatus 70, 100, 400) may provide, at any given time during operation, a signal representative of a rate of flow of the pressurized gas. Such a flow rate may be directly measured, e.g., with a pneumotachometer (see pneumotachometer 134 of apparatus 100 of FIG. 4), or indirectly estimated, e.g., by analyzing changes in: power drawn by; or speed of, the impeller motor (e.g., motor 433).

Figure 15:
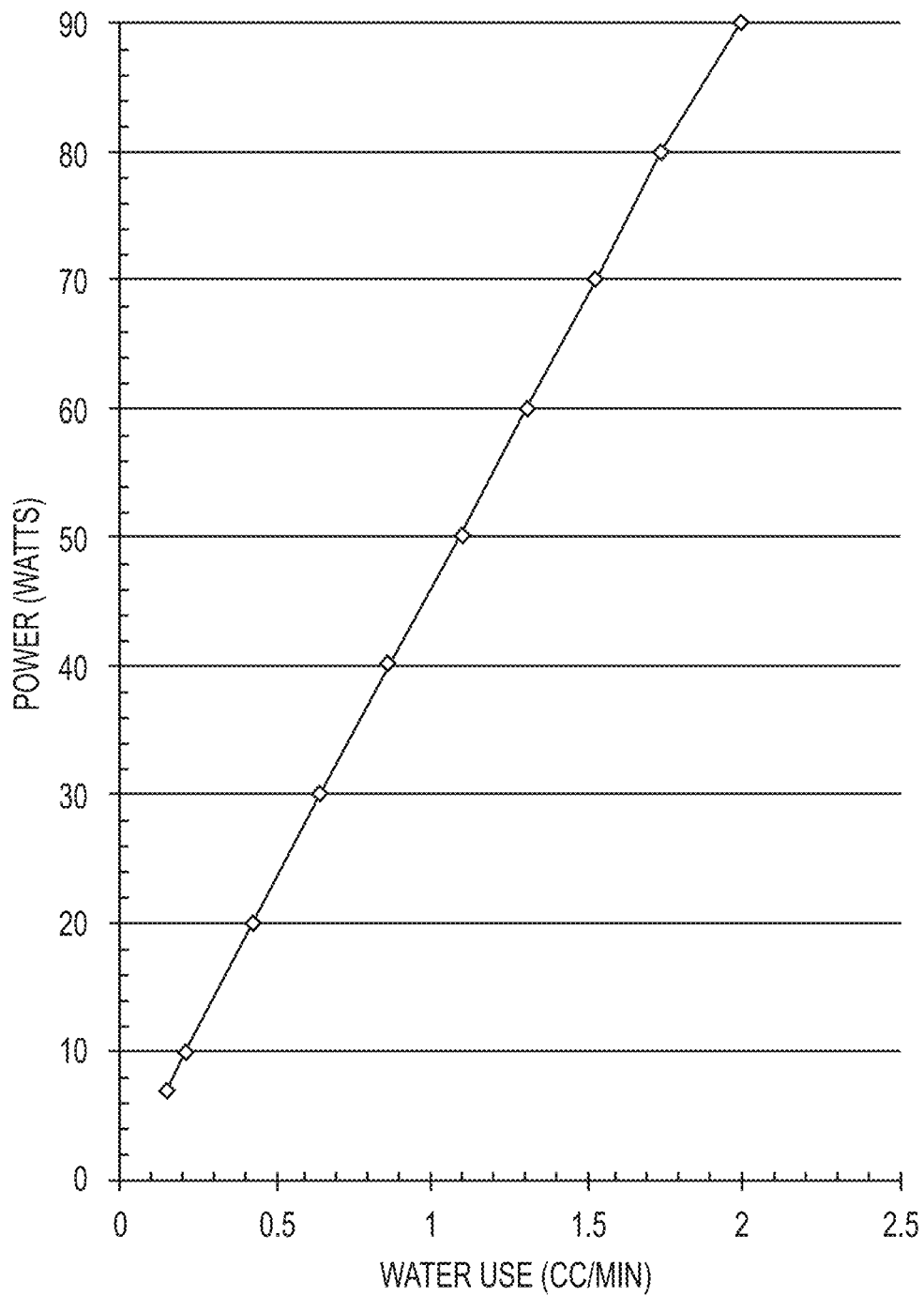
FIG. 15 is a graph of electrical power (watts) used versus water vaporized per minute (cubic centimeters/minute) for a humidifier in accordance with embodiments of the present disclosure.

With this information, power to the CFV (e.g., 302, 602) may be modulated to achieve the constant target humidity level regardless of changes in the rate of flow of the pressurized gas. As an example, in some embodiments, the CFV (e.g., 302, 602) may be based upon a model MyPUREMIST CFV 100 personal humidification unit. FIG. 15 illustrates an exemplary power versus water vaporization performance curve for this particular CFV model. As shown, the CFV may vaporize water in linear proportion to the amount of power provided to the CFV. As a result, the controller (e.g., humidity controller 630) may command the CFV to provide only that amount of humidity needed at any given time by altering the level of electrical power provided to the CFV. The illustrated relationship between power provided to the CFV and the amount of water vaporized (in cubic centimeters/minute (cc/min)) for the CFV may be expressed as:

$$P = (45.3 * F) + 0.6 \quad \text{(Equation 2)}$$

Wherein P is the power in watts provided to the CFV and F is the volumetric flow of water vaporized (in cc/min). The actual power calculated by Equation 2 may include a power efficiency loss factor that may be added as a multiplier (linear or nonlinear), or as an offset factor, to accommodate performance characteristics of any particular CFV or system construction.

Accordingly, in its simplest implementation, apparatus as described herein (e.g., apparatus 70, 100, and 400) may, based upon the instantaneous rate of flow of the pressurized gas detected in the system, energize and modulate the humidifier (e.g., 73, 300, 600) to provide the target humidity level to the user in a continuous modulation humidification mode.

While the vapor produced by the CFV may be proportional to the electrical power provided to the vaporizing device, such a configuration is not limiting. Rather, in other embodiments, most any transfer function, or combination of transfer functions, could define the relationship between electrical power to the CFV and the resulting water vaporized based upon a given CFV design and based upon an apparatus in which the CFV is used. Using the CFV from the model MyPUREMIST CFV 100, power losses may be present and the slope of the curve in Equation 2 may increase with a partial multiplier of this equation.

Figure 16:
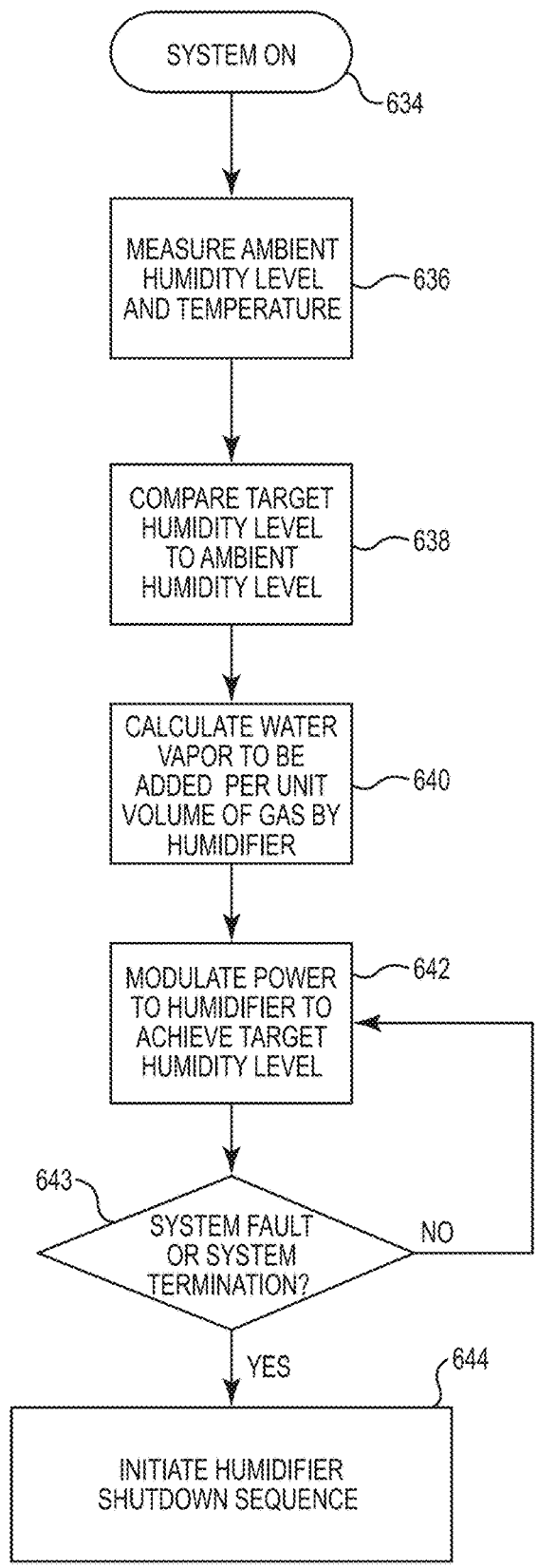
FIG. 16 illustrates a method of operating a PAP apparatus under a continuous modulation humidification mode in accordance with one embodiment.

FIG. 16 is a flow chart illustrating a generalized, exemplary method of operating a PAP apparatus (e.g., apparatus 70, 100, or 400) in the continuous modulation humidification mode. The apparatus may be powered on at 634. During an initialization period, the humidifier (e.g., CFV 602 of the humidifier 600) may remain unpowered so that the apparatus may determine ambient conditions of the gas including humidity level and temperature while the blower is producing the predetermined pressure (e.g., the pressure previously set by the overseeing clinician) at 636. These parameters may be determined via measurement using sensors (e.g., the temperature and humidity sensor 458 (FIG. 12) and relayed to the PAP controller 437 and/or the humidification controller 630. In some embodiments, the pressure could also be measured at this time. In other embodiments, the user may input the approximate temperature and humidity using the joystick 412 and screen 414.

During or before the initialization period, the user may select a desired target humidity level (e.g., using the control interface 410). The apparatus may then compare vapor content of the ambient gas to the target humidity level at 638 and then calculate the difference as the amount of vapor to be added to the flow of pressurized gas at 640. Once this is determined, the controller (e.g., humidification controller 630) may begin modulating power to the humidifier (e.g., to the CFV) to correspondingly modulate humidity added to the flow of pressurized gas in proportion to the rate of flow of the pressurized gas at 642. The rate of flow of the pressurized gas may be provided, in one embodiment, to the humidification controller 630 by the PAP controller (e.g., controller 437). This operation may continue unless a system fault or system termination is detected at 643, at which point the apparatus may initiate a humidifier shutdown sequence at 644.

As stated above, while the continuous modulation humidification mode is effective, humidity of a particular level is of benefit to the user primarily during inspiratory portions of the user's breathing cycles. That is, maintaining a desired target humidity level at the user interface may provide little benefit to the user during expiration. As a result, if the humidity added to the flow of pressurized gas reaching the user interface during expiration were reduced or terminated (e.g., added humidity from the CFV were discontinuous or pulsed), water and power conservation may be realized without negatively impacting the user.

Figure 17:
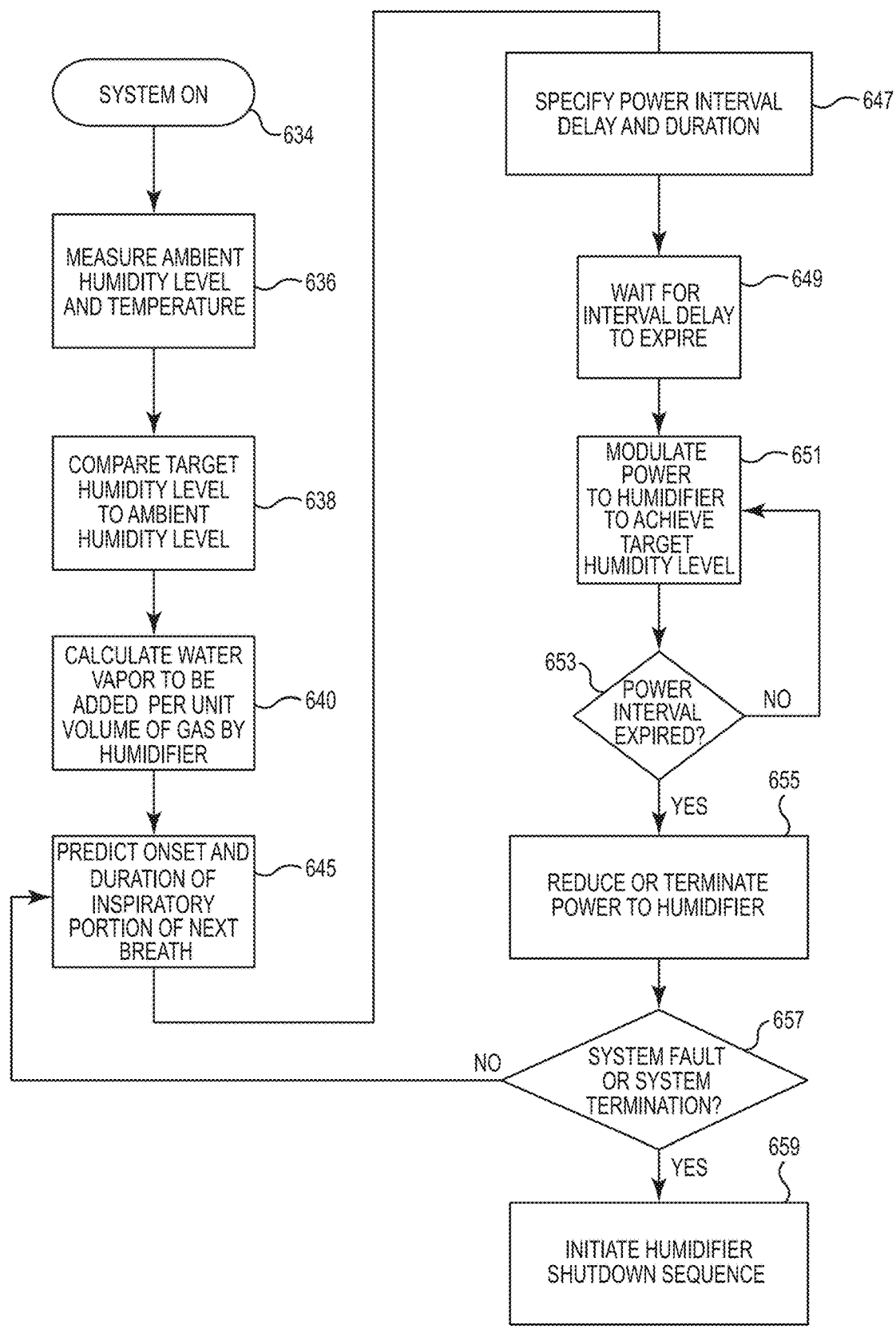
FIG. 17 illustrates a method of operating a PAP apparatus under a discontinuous humidification mode in accordance with one embodiment.

The CFV is positioned remotely from the user interface in the exemplary PAP apparatus 70, 100, and 400. As a result, in order to provide the target humidity level to the user primarily when the user is inspiring requires the PAP apparatus to predict when the added humidity should be injected into the flow of pressurized gas to account for the delay between adding the humidity to the flow of pressurized gas and the flow of pressurized gas with the added humidity reaching the user interface. FIG. 17 illustrates an exemplary method of providing added humidity in such a discontinuous humidification mode.

In general, the process illustrated in FIG. 17 includes steps 634, 636, 638, and 640 already described above with reference to FIG. 16. However, after step 640, the process of FIG. 17 proceeds to step 645. At 645, the controller (e.g., controller 437 or 630) may automatically determine or predict when the onset of the inspiratory phase of the next breath cycle will occur and determine/predict a duration of that inspiratory phase at 645. This prediction may, in one embodiment, be based upon analyzing the current breath cycle or one or more prior or previous breath cycles and anticipating that the next breath cycle will be similar.

Based upon this prediction, the controller (e.g., controller 437 or 630) may automatically select or calculate a power interval start time or delay (e.g., a period of time measured from an indexing event after which power will be provided to the CFV) and power interval duration at 647. "Power interval" or "power interval duration" as used herein refers to the time period in which the controller (e.g., humidification controller) provides electrical power to the humidifier (e.g., to the CFV) at a level that causes the CFV to add humidity (as water vapor) to the flow of pressurized gas. The power interval start time (based upon the power interval delay) and power interval duration are selected or calculated in an attempt to ensure that the flow of pressurized gas with added humidity 140 (see, e.g., FIG. 6) reaches the user interface beginning at or near the onset of the respective inspiratory phases and lasts for most or all of the inspiratory phases (e.g., expires at or near the end or onset of each respective expiratory phase). Once again, the humidification controller may modulate power to the CFV during the power intervals to maintain the target humidity level within the flow of pressurized gas with added humidity even as the rate of the flow of pressurized gas changes. The humidification controller may select or calculate, based upon the time remaining until expected inspiration, the start time and duration of the power interval that will result in: added humidity (at the target humidity level) being provided to the flow of pressurized gas that reaches the mask during inspiration; and a lesser level of humidity (or no added humidity) reaching the mask during expiration (i.e., each flow of pressurized gas with added humidity at the user interface may end at or near the onset of the expiratory phase of its respective breath cycle).

In some embodiments, the power interval delay time is triggered from a start of inspiration. That is, the controller (e.g., controller 437 or 630) may detect when the inspiratory phase of a preceding first breath cycle begins and then initiate the power interval delay and duration for the subsequent target breath cycle based thereon. While described as indexed from the start of inspiration, the power interval delay time could be based upon most any event trigger that occurs during each breath cycle (e.g., start of expiration, peak expiratory or peak inspiratory flow).

After the specified power interval delay elapses at 649, power to the CFV may be initiated (e.g., the power interval may start) and modulated in proportion to the flow of pressurized gas at 651 to achieve the target humidity level. This may continue until the power interval expires at 653, at which point control is passed to 655. At 655, power to the CFV is: reduced to a point where little or no vapor is added to the flow of pressurized gas; or terminated altogether. The process may then determine whether treatment is complete or the PAP apparatus has encountered a fault (e.g., low water reservoir level, CFV fault, low battery (where used) power remaining, etc.) at 657. If not, control may return to 645. Otherwise, a shutdown sequence may be initiated at 659. The shutdown sequence may disable power to the humidifier (e.g., humidifier 600) and may take other steps, e.g., provide a visual or audible alarm.

While these methodologies describe generally how a PAP apparatus may provide continuous or discontinuous humidification modes, the following examples describe more specific implementations.

EXAMPLES

In one example, a computer model was built to simulate different PAP breathing scenarios. For each of these PAP breathing scenarios, humidifier power interval delay (e.g., indexed from a start of inspiration) and power interval duration (e.g., for discontinuous humidification) were then iteratively input into the computer model and the results analyzed. Based upon this analysis, specific values for power interval delay and duration were selected (for each scenario) that yielded the desired target humidity level at the user interface during the inspiratory portion of each breath cycle, and reduced or terminated added humidity to the user interface during the expiratory phase of each breath cycle.

A substantial number of breathing scenarios that might be encountered during typical PAP operation were investigated using the computer model simulation, and corresponding values for power interval delay and duration were iteratively determined for each scenario. These values, could, in one embodiment, be stored, e.g., as a lookup table, within (or otherwise accessible by) the PAP apparatus (e.g., apparatus 70, 100, and 400). Based upon actual sensor measurements and system inputs (e.g., flow, pressure, etc.), the PAP apparatus could then identify the simulation scenario within the lookup table that most closely matches the actual breath cycle and then select the power interval delay and duration values associated with that lookup table entry. Of course, such a system could constantly update the set of parameters being used (and therefore update the power interval delay and duration) to closely follow the user's instantaneous breath cycle.

The exemplary computer model allows for manual input of pertinent system and breath parameters including: hose volume (e.g., hose length and diameter); user interface (mask dead space) volume; intentional leak; PAP pressure; user breath rate; I/E ratio; tidal volume; inspiratory and expiratory flow dynamics/patterns; unintentional leak; ambient humidity and temperature; and target humidity and temperature, among others. With these parameters fixed each scenario, values for power interval delay and duration were manually iterated until the most appropriate humidification values were determined.

Figure 18:
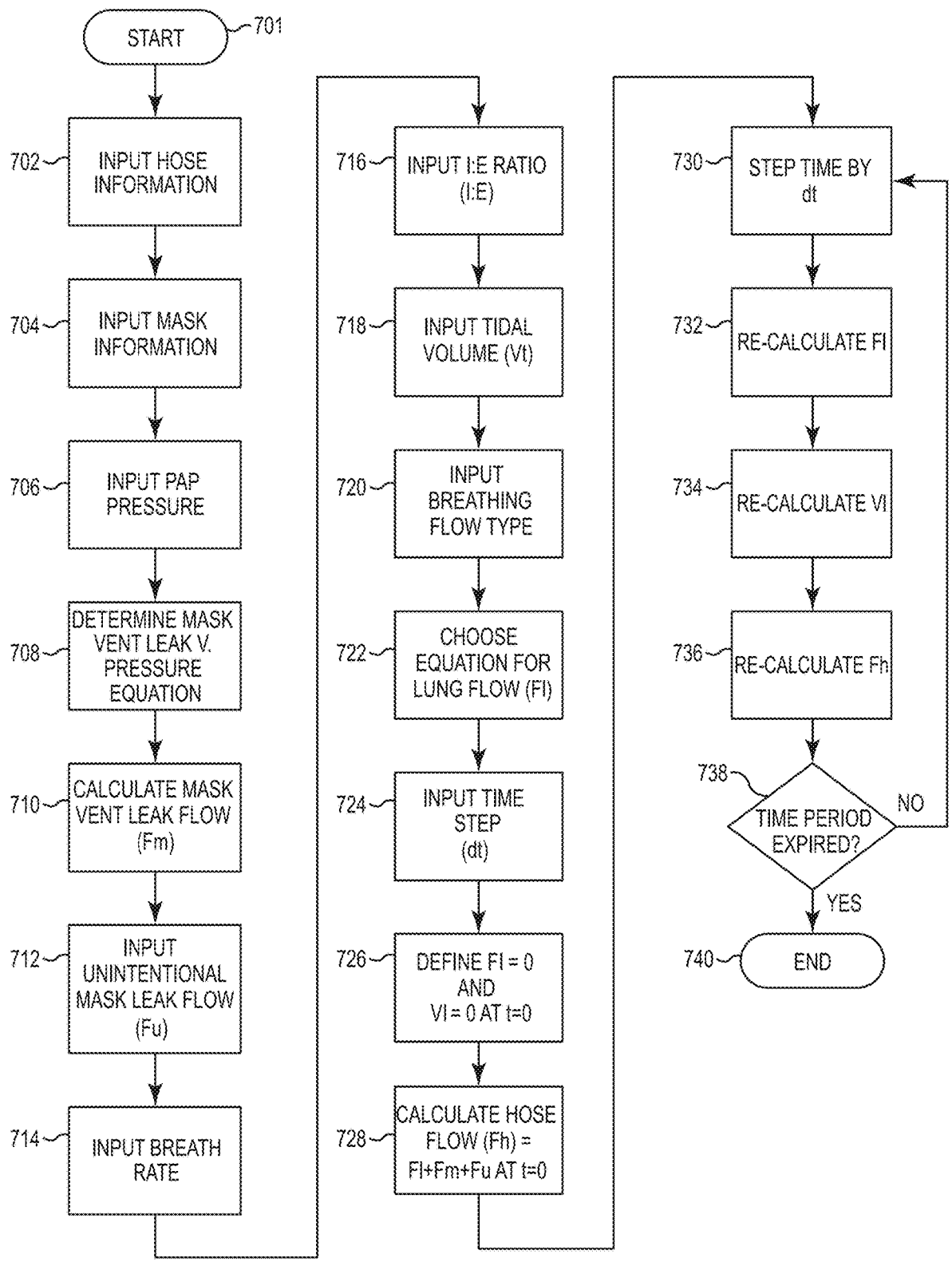
FIG. 18 illustrates a method of simulating flow dynamics in a PAP apparatus.

With reference to FIG. 18, the exemplary computer model may first provide a process for calculating flow dynamics for a particular breathing scenario. For purposes of this discussion, the PAP apparatus may be similar to the apparatus 100 shown in FIGS. 4 and 6. "Flow dynamics" refers to the characteristics (e.g., shape amplitude, breath rate, etc.) of the flow versus time curve.

The process starts at 701. Initial parameters regarding the PAP apparatus may first be provided. For example, hose (e.g., hose 106) information may be input at 702. Hose information may be input as a length and diameter, or directly as a hose volume. Of course, when implemented on an actual PAP apparatus, the hose information could be input into the PAP apparatus as a part number or other hose identifier, from which the PAP apparatus could, e.g., via a lookup table, determine the actual hose volume. Similarly, information regarding the mask (e.g., mask dead space) may be input at 704. Once again, the mask dead space may be provided directly to the PAP apparatus, or the apparatus could determine (e.g., via a lookup table) the dead space based upon a mask part number or other inputted identifier.

The PAP pressure (which is typically determined and set by a clinician) may be input into the model at 706. Based upon the intentional mask leak (which may be part of the mask information inputted at 704), the simulation may determine an appropriate equation or lookup table for mask leak flow versus pressure at 708, and the mask leak flow (Fm) may be calculated at 710.

The model may further have as inputs: an estimated unintentional mask leak flow (Fu) at 712; a breath rate at 714; an inspiratory:expiratory (I:E) ratio at 716; and a tidal volume (Vt) at 718.

The model may also permit the input or selection of one or more breathing types at 720. For example, a sinusoidal breathing pattern may be selected, as well as other predefined shapes. Based upon the breathing type selected for the simulation, an equation may be determined (e.g., selected from a lookup table or otherwise calculated) that represents lung flow (Fl) versus time at 722.

A desired sampling time increment (dt) may be input at 724, and for time (t) set equal to zero, lung flow (Fl) and lung volume (Vl) may be set to zero at 726. Moreover, hose flow (Fh) may be calculated (at time zero) to be equal to the sum of Fl, Fm, and Fu at 728.

The simulation may increment time by dt at 730 and then re-calculate lung flow Fl (at 732), lung volume Vl (at 734), and hose flow Fh (at 736). Assuming that a time period for the simulation has not expired at 738, control will return to 730 as shown and the calculations at 732, 734, and 736 will repeat for each time increment. Once the simulation time period (e.g., a period equal to several breath cycles) has expired at 738, the computer model may end the simulation at 740. The simulation may store the values for lung flow Fl (at 732), lung volume Vl (at 734), and hose flow Fh (at 736) for each time increment dt, along with calculations of: the timing of humidification delivered to the airway relative to the breathing cycle; the power delivered at each time step; and the average power and water consumed over each inspiratory phase, expiratory phase, and complete breathing cycle. By varying the inputs into the computer model and repeating this process, simulation models for dozens, hundreds, or even thousands (or more) of permutations of breathing and system variables (the scenarios) may thus be developed.

Figure 19:
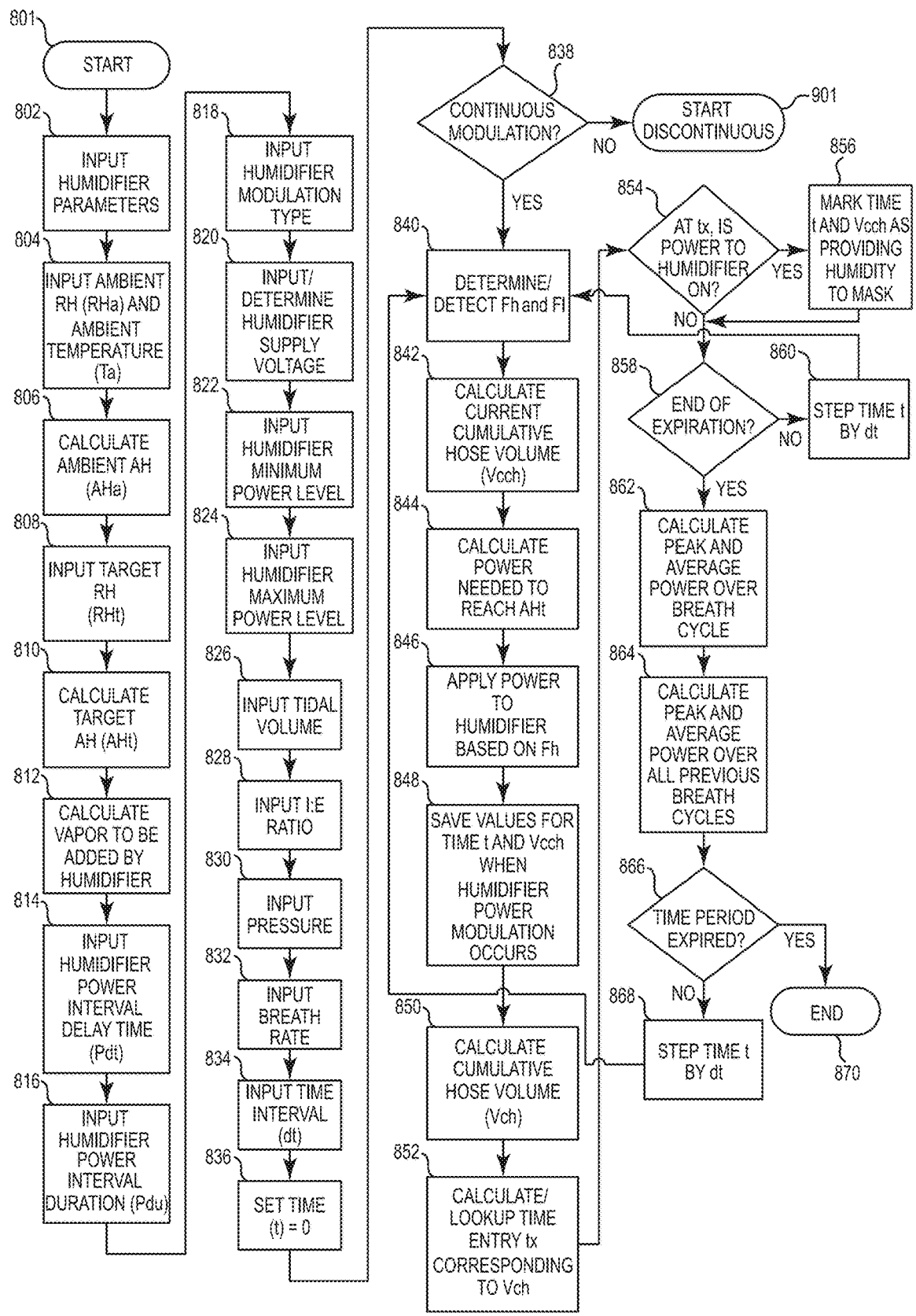
FIG. 19 illustrates a method for providing continuous humidification modulated in accordance with the flow dynamics determined by the method of FIG. 18.

Based upon each breath simulation generated, humidification parameters were then evaluated (while the remaining variables for the simulation remain fixed). As shown in FIG. 19, such an exemplary process may be entered at 801. The computer model may receive, as inputs, various parameters regarding the actual humidifier, e.g., CFV 302 (or 602). In these examples, the humidifier is again the CFV device from a model MyPUREMIST CFV 100. Accordingly, the humidifier parameters entered at 802 may include the power-to-water vaporization equation (see, e.g., Equation 2 above). Other parameters of the CFV, e.g., vaporization initiation delay (e.g., a delay between power delivered to the CFV and emission of vapor) and a vaporization termination delay (e.g., a delay between power termination to the CFV and termination of emission of vapor) may also be input at 802.

The ambient relative humidity (RHa) and ambient temperature (Ta) may be input at 804. With this information, the ambient absolute humidity (AHa) may be calculated (see, e.g., Equation 1 above) at 806. The target relative humidity (RHt) may be input at 808, and the target absolute humidity (AHt) calculated at 810. The difference between the target and ambient absolute humidity (AHt−AHa) may be calculated at 812 to yield the additional vapor to be provided by the humidifier/CFV.

The computer model may be configured to simulate either continuous (e.g., continuous modulation mode) or discontinuous (e.g., discontinuous mode) humidification. For continuous humidification, a power interval delay time (Pdt) may be set to zero at 814, and a power interval duration time (Pdu) may be set to continuous at 816. On the other hand, for discontinuous humidification, a first iterative value for Pdt (e.g., which may be triggered by the onset of inspiration) may be input at 814, while a first iterative value for Pdu may be input at 816. Once again, as will be evident below, the values of Pdt and Pdu can be iteratively revised and the respective simulation re-run for each identified breathing scenario.

In addition to the power interval parameters, the type of power modulation (transfer function) that will be used (e.g., proportional flow modulation, step function input (e.g., square wave), or combinations thereof) may be input at 818.

The supply voltage available to the humidifier may be input or otherwise determined at 820, while the minimum input power level that will be provided to the CFV during operation (e.g. which may be zero watts or something higher) and the maximum input power level to the CFV may be input at 822 and 824, respectively.

The computer model may also receive the following inputs: tidal volume (Tv) at 826; I:E ratio at 828; system pressure (P) at 830; breath rate (e.g., breaths/minute) at 832; and the time interval step (dt) desired at 834. The simulation/system time (t) may then be set to zero at 836 (some of these parameters may have been input earlier, see, e.g., process of FIG. 18).

Control is then routed from 836 to 838. If continuous humidification is selected, the model first determines or detects lung flow Fl and hose flow Fh at 840 (see 732 and 736 in FIG. 18). The model may then calculate a current cumulative hose volume (Vcch) at 842. Vcch, as used herein, is the cumulative volume of gas that the PAP has outputted as of the current time (e.g., may be calculated by integrating hose flow Fl over the elapsed time). The model may then calculate, at 844, the electrical power needed to be supplied to the CFV in order to reach the target ambient humidity level AHt. This electrical power can then be applied to the humidifier (e.g., to the heater of the CFV) based upon the instantaneous hose flow Fh at 846. The computer model may then save the values for time (t) and for the current cumulative hose volume (Vcch) for each time step in which electrical power to the humidifier is being modulated at 848.

Next, the computer model may calculate the cumulative hose volume Vch at 850. As used herein, the cumulative hose volume (Vch) is calculated by subtracting from the current cumulative hose volume (Vcch) the sum of: the hose volume (as measured from the outlet 318 of the humidifier); and the mask volume. For instance, in the system shown in FIG. 4, this subtracted sum would include the volume of the flow path measured from the outlet 318 of the CFV to the face seal of the mask 108. Accordingly, Vch will be less than Vcch at any given time.

The computer model may then, via a lookup table (or calculation), determine a time entry (tx) associated with the calculated value of Vch at 852. If the time entry tx in the lookup table that is associated with Vch specifies that power to the humidifier is on at 854, then the time t and current cumulative hose volume Vcch are tagged as providing humidity to the mask at 856.

If the answer at 854 is no, then the computer model may check to see if the end of the expiratory phase of the current breath cycle has occurred at 858. If not, the time t may be incremented (e.g., by dt) at 860 and control returned to 840 as shown. If, on the other hand, the end of expiration has occurred, then the model may calculate the peak and average power provided to the humidifier over the just-ended breath cycle at 862, as well as the peak and average power utilized over all the previous breath cycles at 864. Of course, given the known relationship between water vapor added by—and power provided to—the humidifier, the average vapor added to the flow of pressurized gas may also be determined. These values may be stored for subsequent utilization.

The computer model may continue by incrementing time by dt at 868 and returning to 840 until an adequate time period (e.g., at least as great as several breath cycles) has expired at 866, in which case the model may end at 870.

Figure 20:
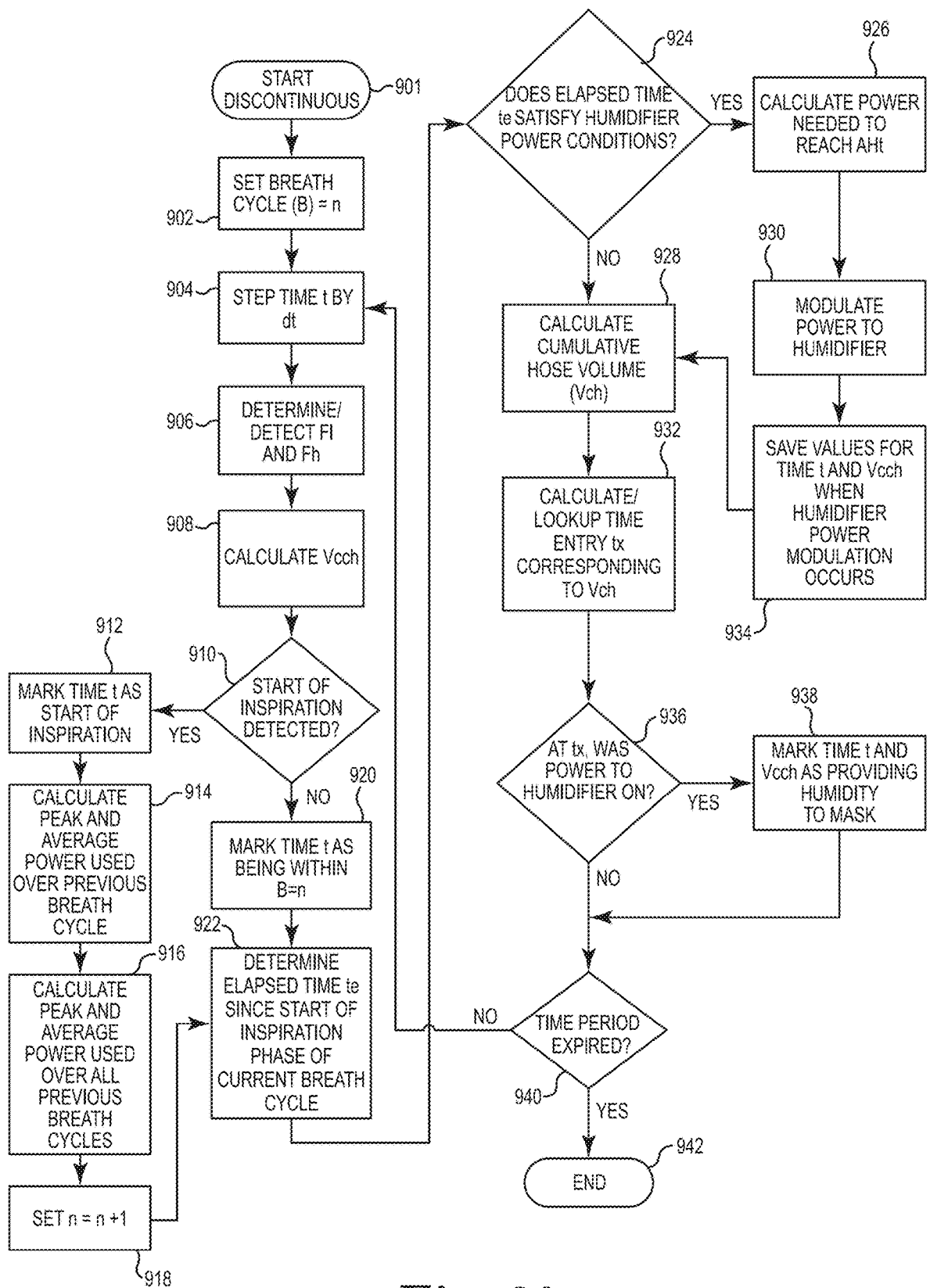
FIG. 20 illustrates a method for providing discontinuous humidification modulated in accordance with the flow dynamics determined by the method of FIG. 18.

If discontinuous humidification is selected (e.g., at 814 and 816 of FIG. 18), then control is passed from 838 in FIGS. 19 to 901 in FIG. 20. A breath cycle counter may set the breath cycle count (B) equal to n (e.g., zero) at 902. After incrementing time by dt at 904, lung flow Fl and hose flow Fh may be determined or otherwise detected at 906. Lung flow Fl may be expressed as a function of breath rate and tidal volume, while hose flow Fl may be expressed as the sum of lung flow and vent flow (the latter which may be expressed as a function of system pressure).

Current cumulative hose volume (Vcch) may be calculated at 908. In some embodiments, Vcch may be calculated by integrating hose flow Fh over the time elapsed. Once again, the model may determine or detect (based upon the flow dynamics) when the inspiratory phase begins at 910. If inspiration is detected at 910, then the time t is tagged as the start of inspiration at 912. The peak and average power used over the just-completed breath cycle, as well as the peak and average power used over all previous breath cycles, may then be calculated at 914 and 916, respectively. The start of inspiration may also result in indexing the breath cycle counter to the next breath cycle (e.g., n+1) as indicated at 918. If the start of inspiration is not detected at 910, then control passes to 920, where the time t is tagged as being within the current breath cycle.

From both 918 and 920, control is passed to 922 to determine the time that has elapsed (te) since the start of inspiration of the current breath cycle was detected at 910. This elapsed time te may be calculated based upon the current time t and the breath rate.

The computer model may then, at 924, determine whether the elapsed time te determined at 922 satisfies two humidifier power conditions: (1) is te greater than or equal to the power interval delay (Pdt; inputted at 814); and (2) is te less than or equal to the sum of the power interval delay (Pdt) and the power interval duration (Pdu; inputted at 816). If so, it is known that the humidifier power is on and control passes to 926. Otherwise, control may pass to 928.

At 926, the computer model may calculate the electrical power needed to provide the flow of pressurized gas with the target ambient humidity (AHt). Based upon the power-to-water vaporization equation and the hose flow Fh (see, e.g., Equation 2), the power to the heating element of the humidifier may then be modulated (e.g., in accordance with the modulation type input at 818) at 930.

The values for time t and current cumulative hose volume Vcch (the latter calculated at 908) may then be saved and marked as being associated with power modulation of the humidifier at 934, after which control may pass to 928. At 928, the cumulative hose volume Vch may be calculated by, as stated above, subtracting from the current cumulative hose volume (Vcch) the sum of: the hose volume (as measured from the outlet 318 of the humidifier); and the mask volume.

Once Vch is determined, a time entry tx (e.g., from a lookup table or calculation) that corresponds to that value of Vch (or the next largest value of Vch) is determined at 932. The lookup table can then determine, for this time entry tx value, whether the humidifier power is on or off at 936. If the answer at 936 is yes, then the time t and Vcch are marked as occurring while humidity is provided to the mask at 938. In either event, control is passed to 940. If the simulation time period has expired, the process may then end at 942. Otherwise, control may return to 904 as shown.

As indicated above, in the illustrated examples, the power interval delay time is indexed from the beginning of the inspiratory phase of each breath cycle (the "indexing event"). However, such a configuration is not limiting. For instance, peak inspiratory flow, inspiratory lung volume, peak expiratory flow, and expiratory lung volume, among others, could each be used as the indexing event.

Once again, for any given set of breathing and physical conditions (i.e., for any one of the scenarios modelled), multiple simulations were run that iteratively covered a range of humidifier conditions (e.g., a range of power interval delays and power interval durations) while all other variables remain constant. These iterations were then evaluated to identify the values of Pdt and Pdu that provided the desired target humidity level at the user interface during most or all of each inspiratory phase of each scenario, but provided less or no added humidity to the flow of pressurized gas at the user interface during each expiratory phase. Once the best solution to each scenario was determined, a lookup table of power interval delay and power interval duration times was constructed and indexed to the respective scenarios. Such a lookup table may be similar to that shown in Table I. below, wherein for each scenario, Pdt and Pdu are tabulated.

TABLE I

| Breathing Scenario | Power Interval Delay, seconds | Power Interval Duration, seconds |
|---|---|---|
| 1 | Pdt(1) | Pdu(1) |
| 2 | Pdt(2) | Pdu(2) |
| 3 | Pdt(3) | Pdu(3) |
| n | Pdt(n) | Pdu(n) |

In evaluating the iterative results to create each record in the lookup table, various characteristics of the simulations may be analyzed. These include, among others: how much humidity is delivered to the user interface during inspiration; what is the duration of the humidity delivered relative to the duration of the inspiratory phase; how much added humidity is provided at the user interface during expiration; and what is the relative humidity at the user interface compared to the target relative humidity. As discovered, a solution may exist for many breathing scenarios that provides the desired target humidity during inspiration, while reducing or terminating added humidity during expiration.

The lookup table (e.g., Table I) could be incorporated into an actual PAP apparatus (e.g., 70, 100, or 400). The PAP apparatus (e.g., its controller(s)) could then continuously monitor parameters such as lung flow and hose flow (among others) and compare them to the breathing scenarios contained in the lookup table to determine which table entry is most appropriately matched to the current (e.g., measured) flow pattern. Once found, the appropriate power interval delay and duration values Pdt and Pdu from that table entry could be used to control the CFV and provide the desired humidification. Of course, the controller(s) may update these parameters in real time, e.g., every calculation cycle, to ensure that the most accurate humidification parameters are being used throughout the treatment period.

In other embodiments, the simulation (or the PAP and/or humidification controller) may include the capability to automatically predict an appropriate power interval delay and power interval duration for a given breathing scenario without requiring the manual iterations described above. For example, the simulation (or controller) may accept any of the input or determined parameters described above with respect to FIGS. 18-20. However, instead of inputting specific breathing characteristics and flow dynamics, the system (e.g., PAP apparatus) may measure these parameters during each breath cycle and then, based upon calculations using those parameters, predict a power interval delay (Pdt) and power interval duration (Pdu) for the now-current or next breath cycle that achieves the desired humidification goal. Once again, such a simulation model could be programmed directly into the PAP and/or humidification controllers to calculate directly the power interval delay and duration without the need for lookup table entry matching. Of course, the controller(s) could again update these parameters in real time, e.g., every calculation cycle, to ensure that the most accurate humidification parameters are being used throughout the treatment period.

Figure 21:
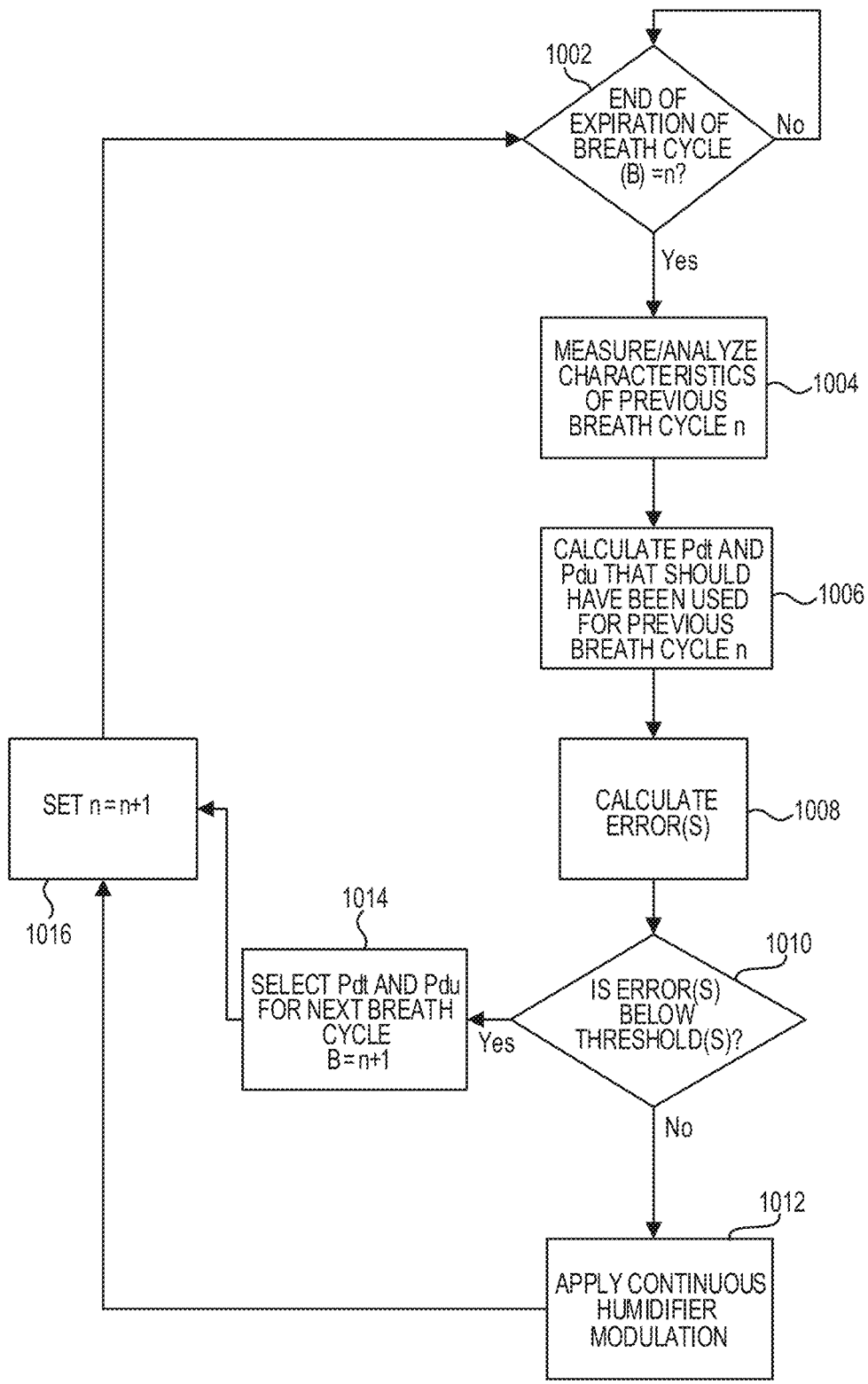
FIG. 21 illustrates a method for predicting humidification timing in accordance with one embodiment of the disclosure.

One embodiment that utilizes a predicted/calculated power interval delay and duration is illustrated generally in FIG. 21. As shown in this view, the end of the expiratory phase of a breath cycle "n" (e.g., which corresponds with the beginning of a subsequent breath cycle "n+1") may be detected at 1002 based upon any number of methods. The simulation may then measure/analyze characteristics of the previous breath cycle n at 1004. For example, the characteristics analyzed may include breath rate, I:E ratio, breath waveform, flow, volume, pressure, and/or other breathing parameters.

Based upon an analysis of these characteristics of the breath cycle n, ideal values for power interval delay (Pdt) and power interval duration (Pdu) that would have provided effective humidification (e.g., provided power to the CFV in a way that would have produced the desired humidity level at the mask for most or all of the inspiratory phase while providing little or no additional humidity at the mask during the expiratory phase) during the breath cycle n may be calculated at 1006.

These ideal values of Pdt and Pdu calculated at 1006 may then be compared, in one embodiment, to the actual values of Pdt and Pdu that were used during the breath cycle n, and a difference or error calculated at 1008. In some embodiments, similar error calculations may be made comparing the ideal values of Pdt and Pdu calculated at 1006 to average values of Pdt and Pdu for two or more previous breaths. In yet other embodiments, error calculations may be generated based upon: the previous breath, the previous two breaths, and on up to the previous x breaths (where x is greater than or equal to three).

If it is found at 1010 that one or more of the errors calculated at 1008 exceeds a threshold value, control may pass to 1012, wherein a continuous modulation humidification mode is activated, after which the breath count B is indexed at 1016, and control returns to 1002. The continuous modulation humidification mode may remain active until breathing has stabilized, which may be determined by the errors calculated at 1008 dropping below the threshold values at 1010. The threshold value of error may be based upon some predetermined criteria that suggests breathing has become too erratic to permit accurate prediction of Pdt and Pdu.

If, on the other hand, the error determination at 1010 is below the established threshold error level, control may pass to 1014. Based upon the error calculations made at 1008, values of Pdt and Pdu may be selected/predicted for the next (now-current) breath cycle (n+1) at 1014. For instance, the values of Pdt and Pdu for the next breath cycle may be based upon the lowest error calculated at 1008. Alternatively, the various errors calculated at 1008 may be averaged and used to predict Pdt and Pdu for the next breath cycle.

After selecting Pdt and Pdu, the breath cycle counter may be indexed to reflect the actual breath cycle count at 1016, after which control is returned to 1002.

Thus, in some embodiments, the simulation (or the PAP or humidification controller) may at the end of each breath cycle, calculate an optimal or ideal power interval delay and power interval duration for that just-completed breath cycle and compare those values to the predicted values that were actually used during the just-completed breath cycle (and/or to one or more other preceding breath cycles) to generate one or more errors for both Pdt and Pdu. In the event that one or more of those calculated errors exceeds a threshold, the process may resort to continuous power modulation (continuous modulation humidification mode) until the calculated error(s) returns to acceptable levels.

Error calculation (see, e.g., 1008 in FIG. 21) may be based upon one or more levels of testing. For instance, the values of Pdt and Pdu may be compared to the corresponding values of the immediately preceding breath, and/or on the corresponding values from two or more previous breaths. In the case of the latter, the errors from the two or more previous breaths may be analyzed and the lower error values used to predict the power interval delay and duration for the next breath.

While described as a simple average, other embodiments may calculate error based upon a more sophisticated statistical analysis. For instance, other embodiments may calculate error based upon weighted or moving averages, standard deviations, trend analyses, etc. where such analyses are beneficial to the accurate prediction of Pdt and Pdu.

As the process of FIG. 21 demonstrates, operation may default to providing the desired humidity level via the continuous modulation humidification mode when the PAP system (e.g., controller(s)) is unable to accurately predict Pdt and Pdu by setting Pdt to zero and Pdu to continuous duration. Such a feature may be advantageous for many users and situations, e.g., those who experience numerous periods of unstable breathing over the course of the treatment period, those transitioning between sleep stages, and those changing body positions.

In addition to predicting Pdt and Pdu based upon an analysis of one or more previous breaths, systems/methods like those described above and shown in FIG. 21 may, at any time during a breath cycle, if any breathing parameter is found not to be following the expected course, utilize current, real-time measurements to recalculate the power interval delay and duration instead of waiting until the end of each expiration. In this way, the simulation model (or actual PAP measurements) may function as a test of prediction accuracy, wherein the system may ultimately fallback to continuous modulation humidification mode in the event that prediction accuracy deviates from a predetermined threshold.

Figure 22B:
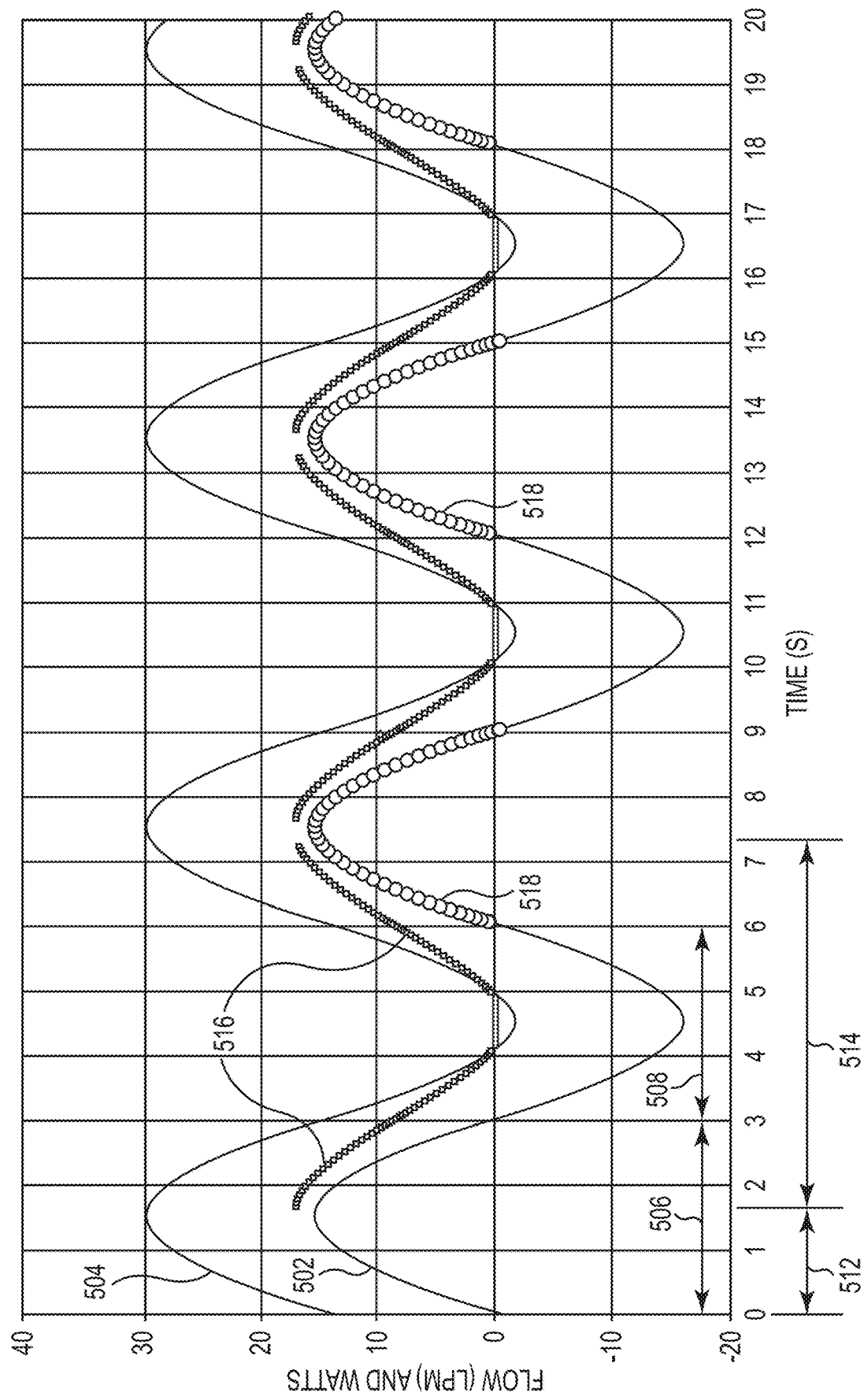
Figure 22C:
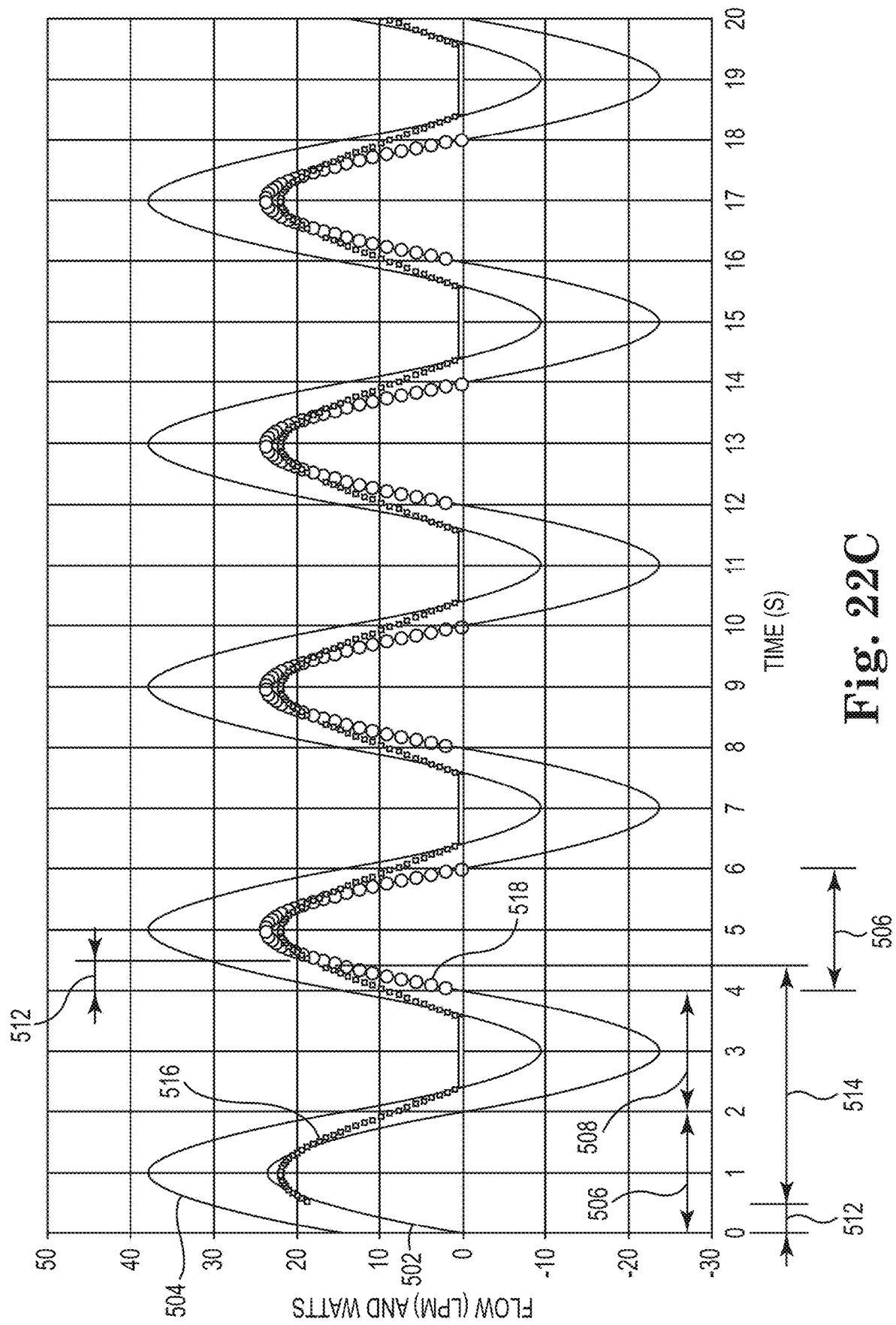

Breathing scenarios using predicative humidification concepts and real-time, controller-calculated values for power interval delay and duration (as described above with reference to FIG. 21) are shown in FIGS. 22A-22C for certain situations having stable breathing patterns. FIGS. 22A-22C illustrate computer-generated simulations of various breathing scenarios and how such scenarios may be accommodated by PAP and humidification systems and methods in accordance with embodiments like those described herein. As evident from these figures, PAP systems and methods may, based upon an analysis of various breathing parameters, predict when to provide power to the CFV (e.g., determine the power interval delay time) and when to de-energize or substantially reduce electrical power to the CFV (e.g., the power interval duration), as well as how to modulate the electrical power to the CFV during operation. As a result, providing a flow of pressurized gas having a generally constant level of humidity at the user interface 108 during inspiration (regardless of gas flow rate), and reducing or even terminating the added humidity to the flow of pressurized gas at the user interface during expiration, may be achieved for many typical PAP breathing scenarios.

The simulations of FIGS. 22A-22C are based upon a system configured as shown generally in FIGS. 4 and 6, and are for a constant pressure PAP (CPAP) apparatus. Each simulation assumes: the distance 320 (see FIG. 6) between the CFV 302 and the user interface 108 is 72 inches (183 centimeters) and that the delivery tube has an inner diameter of 21 mm; a hose volume of 633 cc; a mask dead space or volume of 100 cc; and an intentional leak of 4 mm (i.e., the vent 114 provides a port size equivalent to a hole of 4 mm in diameter).

Moreover, tidal volume is assumed to be 500 cubic centimeters (cc); the ambient temp is 23 degrees C.; the ambient relative humidity is 40%; the target relative humidity is 90%; the I:E ratio is 1:1; and a power efficiency factor of the CFV is 1.25. The simulations seek to deliver added vapor to achieve the target humidity level during the entire inspiratory portion of each breath cycle. With these assumptions, FIG. 22A illustrates a simulation at a PAP pressure of 20 centimeters (cm) of water and a breath rate of 10 breaths/minute (i.e., a breath period of six seconds); FIG. 22B is a simulation at a PAP pressure of 4 cm of water and a breath rate of 10/breaths/minute; and FIG. 22C is a simulation at a PAP pressure of 4 cm of water and a breath rate of 15 breaths/minute (breath period of 4 seconds).

As already discussed above, the simulation model measured or calculated several parameters (the "measured or calculated system parameters"). These measured or calculated system parameters may be measured/calculated based upon sampling at some time interval (e.g., every 10-50 milliseconds). Any or all of these calculated parameters may be continuously updated and stored for operational use or subsequent clinician interrogation. These measured or calculated system parameters may include: total hose flow (e.g., intentional leak, unintentional leak, and breath flow); breath rate; inspiratory tidal volume; expiratory volume; I:E ratio; inspiratory and expiratory flow dynamics (e.g., parameters representing the shape of inspiratory or expiratory flow versus time); a start and an end of the inspiratory portion of each breath cycle; a start and an end of the expiratory portion of each breath cycle; the time of peak inspiratory flow; and the time and peak expiratory flow. PAP pressure may also be included as measured or calculated parameter.

A plot of an exemplary simulation model is illustrated in FIG. 22A. As shown in this figure, a sinusoidal first curve 502 represents lung flow, while a sinusoidal second curve 504 represents total flow (e.g., hose flow) in the delivery conduit 107 (lung flow plus intentional leakage through vent 114 (see FIG. 4) plus estimated unintentional leak flow). The first and second curves 502, 504 are generally identical, but offset by the amount of the leak, which is about 32 liters/minute in this simulation. A first, e.g., inspiratory, portion 506 of the lung flow curve represents the inspiration phase of the breath cycle 510, while a second, e.g., expiratory, portion 508 of the lung flow curve represents the expiratory phase of the breath cycle. Of course, consecutive portions 506 and 508 together define a single breath cycle 510 (the suffixes "-1," "-2,", "-3," etc. of reference numeral 510 represent distinct breath cycles, e.g., breath cycle 510-1 is an initial breath cycle, breath cycle 510-2 immediately follows breath cycle 510-1, breath cycle 510-3 immediately follows breath cycle 510-2, etc.).

As described earlier, the simulation model may be capable of determining or calculating a variety of breath parameters. Based on various measurements or inputs of tidal volume and pressure, the controller (e.g., controller 303 of FIG. 4) may calculate the power interval delay (Pdt) 512 to be applied beginning at the initiation of each inspiration. In the scenario shown in FIG. 22A, the power interval delay 512 is 3.85 seconds. In general, the power interval delay 512 correlates an activity at the user interface 108 (e.g., inspiration) with an operation of the CFV 302 (e.g. vapor emission), the latter being located the distance 320 upstream from the user interface 108. Stated another way, the power interval delay 512 may be calculated or selected, based on various system parameters, to ensure that vapor is introduced into those portions of the flow of pressurized gas that will ultimately reach the user interface 108 as the user begins to inhale. While shown as being triggered by the beginning of an inspiratory phase of a breath cycle, this trigger (initialization of the power interval delay) could be based upon other breath parameters as indicated herein.

Moreover, the computer model may simulate the application of power (see, e.g., CFV power curve 516, further described below) to the CFV 302 for a power interval duration or period 514 (Pdu) as illustrated in FIG. 22A. The power interval duration 514 may be selected to ensure that the flow of pressurized gas with added humidity delivered at the user interface at the beginning of inspiration continues for most or all of the inspiratory phase 506 of each breath cycle 510, yet is reduced or suspended during the expiratory phase 508. In the embodiment illustrated in FIG. 22A, the power interval duration is 4.05 seconds. In FIG. 22A, the sections 518 of the inspiratory phases of the breath cycles 510-2 and 510-3 (curve 502) indicates when the humidity added by the CFV reaches the user interface based upon the model simulation. As shown in this view, by delivering power to the CFV in accordance with the power curve 516, the added humidity reaches the user interface for most of the inspiratory portion of each breath cycle, while little or no added humidity reaches the user interface during the expiratory phase.

In addition to turning power to the CFV 302 on and off (or at least reduced to a minimum threshold power), simulated power to the CFV may be modulated during use as represented by the power curve 516 in FIG. 22A. That is, power to the CFV 302 may be modulated in proportion to the flow rate of the gas in the system such that vapor content of the humidified gas remains relatively constant even as the flow of pressurized gas moving past the CFV 302 changes. For example, in FIG. 22A, the power to the CFV 302 varies from about 9.7 watts (w) to about 27 w, during the power interval. Moreover, in this simulation, for any given breath period, the CFV is inactive (e.g., unpowered) for about 1.95 seconds, yielding an average per breath cycle wattage utilized of about 12 w. The actual humidity level attained may be dependent on many factors. However, in this case, 0.58 watts/liter of gas flow per minute is estimated to raise the relative humidity from 40% to 90% at an ambient temperature of 23 degrees C., taking into account the CFV inefficiencies of the particular configuration. The actual wattage may vary based upon, for example, the efficiency of the CFV, the ambient temperature, and the heat energy lost from the CFV to the surrounding structure and air.

Results similar to that illustrated in FIGS. 22A-22C were observed using a bench test apparatus similar in many respects to the apparatus 100 of FIG. 4. The test apparatus included simulated breathing loads at the mask, and included various sensors (e.g., at the mask 108) to confirm accuracy of the various humidification prediction methods described herein (e.g., wherein power interval delay and duration were determined iteratively or, as shown in FIGS. 22A-22C, were calculated automatically in real time by the controller).

FIG. 22B illustrates a scenario simulation plot similar to FIG. 22A (i.e., tidal volume (500 cc) and breath rate (10 breaths/minute) being the same), but with PAP pressure set to 4 cm of water. As shown in this view, the power interval delay 512, power interval duration 514, and power curve 516 (e.g., average power/cycle and maximum power/cycle) may change as shown in Table II.

FIG. 22C illustrates a scenario simulation plot similar to FIG. 22B (PAP pressure is set to 4 cm of water, tidal volume is 500 cc), except that the simulated breath rate is at 15 breaths per minute (a breath period of 4 seconds). Table II again shows the values determined/calculate for this specific simulation.

TABLE II

| PAP Pressure, cm of water | Power Interval Delay, seconds (512) | Power Interval Duration, seconds (514) | Average power/cycle, watts | Peak power/cycle, watts | Minimum power/cycle, watts |
|---|---|---|---|---|---|
| 20 (FIG. 22A) | 3.85 | 4.05 | 12.1 | 27.3 | 0 |
| 4 (FIG. 22B) | 1.65 | 5.6 | 8.5 | 17.3 | 0 |
| 4 (FIG. 22C) | 0.55 | 3.9 | 11.2 | 21.7 | 0 |

Accordingly, it can be seen from these computer simulations how an exemplary PAP apparatus 100 could accommodate a wide variety of system pressures while still providing the benefit of precise vapor delivery with minimal power required. Moreover, as shown in FIGS. 22A-22B, as the system pressure drops (with other breathing parameters being equal), the power interval delay and power may decrease, while the power interval duration may increase. At one point, see, e.g., FIG. 22B, the power curve 516 may drop to zero (e.g., at peak expiration). This could indicate that simulated flow has actually reversed in the delivery conduit 107.

While these simulations indicate that an exemplary PAP apparatus (e.g., apparatus 100) may accommodate different breathing scenarios while still providing the desired vapor delivery, certain scenarios may present issues. For example, the ability to deliver vapor to the user during the entire inspiratory phase of each breath cycle could be adversely affected by: low breath rates; high leaks (intentional and unintentional); and low PAP pressures. For example, in the simulation of FIG. 22C, humidified gas (portions 518 of inspiratory phase 506) may lag inspiration slightly. This issue may become more pronounced in other scenarios. However, the goal of providing humidity to the user during inspiration while reducing humidity during other portions of the breath cycle may still be generally achieved. Moreover, should the timing of delivery of humidified gas to the user interface shift too far from the intended inspiratory phase, apparatus and methods as described herein may revert to the continuous modulation humidification mode until the system can again accurately provide the desired discontinuous humidification mode. In still other embodiments, vapor delivery could be suspended entirely during a portion of the treatment period where such suspension would be beneficial.

As one may appreciate, these simulations illustrate exemplary implementations for predictive PAP humidification. When a sufficient number of these simulations are developed, a lookup table (containing scenario variables and their corresponding values for power interval delay and power interval duration) may be generated and stored in an actual PAP apparatus. During operation, the PAP apparatus controllers may match the actual breath parameters to the lookup table to find appropriate values for power interval delay and duration. Alternatively, the methods described with respect to FIG. 21 may be used to calculate these variables based on measured breath parameters in real-time.

While exemplary transfer function relationships between CFV power and vapor produced are referenced above (see, e.g., Equation 2), such functional relationships may change to address the influence of various factors. For instance, it was discovered that the CFV is very responsive when the heater is maintained at a temperature just below its vaporization temperature. Therefore, in order to maximize response time, it may be preferred to maintain power at a minimum threshold power level (e.g., hold power at 5 watts rather than terminating power altogether) and modulate power proportional to flow above that level during the power interval. In other embodiments, the transfer function may deviate from strict modulation based upon the flow rate of the gas. For example, at the beginning of the power interval, it may be beneficial to momentarily spike the power to a high level to introduce water vapor more quickly. The power level may then return to levels dictated by the flow modulation relationship.

In practice, accuracy of the simulation models could be confirmed and corrected by including a humidity and temperature sensor in the mask to provide a specific measurement of the humidity and temperature during the inspiratory portion of each breath cycle. By relaying this information to the PAP controller and/or the humidification controller, humidification parameters may be tuned during PAP operation.

While described herein above in the context of a CPAP device, it is contemplated that the same or similar algorithms utilized to time the delivery of the humidified gas to the user interface could also be adapted to function with other PAP devices such as Bi-Level and Auto-titrating systems. At a minimum, computer algorithms may be modified to utilize pressure as a variable rather than a constant in these Bi-PAP and Auto-PAP systems.

U.S. Pat. No. 8,074,645 is incorporated herein by reference in its entirety. Moreover, the complete disclosure of other patents, patent documents, and publications cited in the Background, the Detailed Description of Exemplary Embodiments, and elsewhere herein are incorporated by reference in their entirety as if each were individually incorporated.

Illustrative embodiments are described and reference has been made to possible variations of the same. These and other variations, combinations, and modifications will be apparent to those skilled in the art, and it should be understood that this invention is not limited to the illustrative embodiments set forth herein.

What is claimed is:

1. A method for adding humidity to gas delivered by a positive airway pressure apparatus, the method comprising:
producing, with a blower, a flow of pressurized gas at a variable flow rate;
transporting the flow of pressurized gas from the blower to a user interface via a delivery tube positioned between the blower and the user interface;
detecting, with a controller, one or both of an inspiratory phase and an expiratory phase of one or more breath cycles;
introducing, during a power interval, humidity into a portion of the flow of pressurized gas to produce a discrete flow of pressurized gas with added humidity, the humidity introduced by a vaporizing device having an outlet proximate the blower and in communication with the flow of pressurized gas; and
determining, automatically with the controller, a start time and duration of the power interval so that the flow of pressurized gas with added humidity reaches the user interface at or near an onset of an inspiratory phase of a current or future breath cycle and ends at or near an end of the inspiratory phase, or at or near an onset of an expiratory phase, of the current or future breath cycle, wherein determining the start time and duration of the power interval comprises:
measuring one or more characteristics of a previous breath cycle;
determining ideal values of the start time and duration of the power interval for the previous breath cycle;
comparing the ideal values of the start time and duration of the power interval for the previous breath cycle to actual values of the start time and duration used;
calculating an error between the ideal values and the actual values of the start time and duration of the power interval for the previous breath cycle; and
predicting the start time and duration of the power interval for the current or future breath cycle based at least in part upon the error calculated.

2. The method of claim 1, further comprising introducing the humidity periodically into the flow of pressurized gas to produce periodic flows of pressurized gas with added humidity, wherein each of the periodic flows of pressurized gas with added humidity is timed to reach the user interface at or near the onset of an inspiratory phase of one of the one or more breath cycles.

3. The method of claim 1, wherein introducing the humidity into the flow of pressurized gas for the power interval comprises providing electrical power to the vaporizing device during the power interval.

4. The method of claim 3, wherein providing the electrical power to the vaporizing device during the power interval comprises modulating the electrical power to the vaporizing device during the power interval.

5. The method of claim 1, wherein determining the start time and duration of the power interval comprises analyzing one or more characteristics of the one or more breath cycles preceding the current or future breath cycle.

6. The method of claim 1, wherein introducing the humidity into the portion of the flow of pressurized gas comprises introducing water vapor into the flow of pressurized gas at a variable rate proportional to a flow rate of the flow of pressurized gas.

7. A method for adding humidity to gas provided by a positive airway pressure (PAP) apparatus, the method comprising:
producing a continuous and variable flow of pressurized gas with a blower;
transporting the flow of pressurized gas from the blower to a user interface via a delivery tube positioned between the blower and the user interface;
predicting, automatically with a PAP controller, a start time and duration of an inspiratory phase of a target breath cycle based upon an analysis of a preceding breath cycle;
calculating or selecting, automatically with a humidification controller, a delay time and duration of a power interval by: comparing ideal values of the delay time and duration of the power interval for the preceding breath cycle to actual values of the delay time and duration used; calculating an error between the ideal values and the actual values of the delay time and duration of the power interval for the preceding breath cycle; and predicting the start time and duration of the power interval for the target breath cycle based at least in part upon the error calculated;
providing power, under control of the humidification controller, to a vaporizing device after expiration of the power interval delay time, the power lasting for the power interval duration, wherein the vaporizing device is located proximate an outlet of the blower and is in communication with the flow of pressurized gas; and
introducing humidity with the vaporizing device into the flow of pressurized gas during the power interval duration to produce a flow of pressurized gas with added humidity that reaches the user interface at or near an onset of the inspiratory phase of the target breath cycle and terminates at or near a beginning of an expiratory phase of the target breath cycle.

8. The method of claim 7, further comprising modulating the power provided to the vaporizing device in proportion to a flow rate of the flow of pressurized gas during the power interval duration such that a near constant humidity level is maintained in the flow of pressurized gas with added humidity.

9. The method of claim 7, wherein one or both of the delay time and duration of the power interval are selected based, at least in part, upon one or more of: a pressure of the flow of pressurized gas; an intentional leak; an unintentional leak; a breathing flow; a breath rate; an inspiratory tidal volume; an expiratory volume; an I:E ratio; inspiratory and expiratory flow dynamics; start and end of inspiration; start and end of expiration; time of peak flow during inspiration; time of peak flow during expiration; ambient temperature; ambient humidity; an output power available to the vaporizing device; a power-to-vaporization transfer function of the vaporizing device; and a distance between an outlet of the vaporizing device and the user interface.

* * * * *